(12) United States Patent
Ohguri

(10) Patent No.: US 11,709,283 B2
(45) Date of Patent: Jul. 25, 2023

(54) RADIOGRAPHY SYSTEM

(71) Applicant: CANON KABUSHIKI KAISHA, Tokyo (JP)

(72) Inventor: Hirokazu Ohguri, Chiba (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 108 days.

(21) Appl. No.: 17/504,089

(22) Filed: Oct. 18, 2021

(65) Prior Publication Data
US 2022/0035054 A1  Feb. 3, 2022

Related U.S. Application Data

(63) Continuation of application No. PCT/JP2020/011186, filed on Mar. 13, 2020.

(30) Foreign Application Priority Data

Apr. 25, 2019  (JP) ................. 2019-084431

(51) Int. Cl.
*G01T 1/175* (2006.01)
*G01T 1/20* (2006.01)
*G01T 1/24* (2006.01)

(52) U.S. Cl.
CPC ............ *G01T 1/175* (2013.01); *G01T 1/2006* (2013.01); *G01T 1/247* (2013.01)

(58) Field of Classification Search
CPC ....... G01T 1/175; G01T 1/2006; G01T 1/247; G01T 7/00; A61B 6/00; H02J 7/00; H02J 50/10; H02J 50/80; H02J 50/90; H04N 5/32; H04N 25/709
See application file for complete search history.

(56) References Cited

U.S. PATENT DOCUMENTS

| 8,080,802 B2 | 12/2011 | Nishino |
| 8,654,926 B2 | 2/2014 | Ohta |
| 9,380,988 B2 | 7/2016 | Kitano |

(Continued)

FOREIGN PATENT DOCUMENTS

| JP | H03285299 A | * 12/1991 |
| JP | 2008-206219 A | 9/2008 |

(Continued)

OTHER PUBLICATIONS

Deeapareshikaa et al., "Design of uninterruptible power supply power control system equipped mobile digital radiography,", International Conference on Communication and Signal Processing, 4 pages, India. (Year: 2017).*

*Primary Examiner* — Kiho Kim
(74) *Attorney, Agent, or Firm* — Venable LLP

(57) ABSTRACT

A radiography system comprising a radiography device and a power supply device is provided. The radiography device includes a sensor unit for obtaining a radiographic image and is capable of non-contact power reception, and the power supply device is capable of non-contact power supply to the radiography device. In a period in which a fluctuation in a power supply frequency of the power supply from the power supply device to the radiography device affects a signal obtained by the radiography device from the sensor unit, the power supply device supplies power to the radiography device at a constant power supply frequency.

20 Claims, 15 Drawing Sheets

(56) References Cited

U.S. PATENT DOCUMENTS

| | | | |
|---|---|---|---|
| 10,466,373 B2 | 11/2019 | Ohguri | |
| 2002/0024601 A1* | 2/2002 | Kaifu | H04N 5/325 |
| | | | 348/241 |
| 2013/0102245 A1 | 4/2013 | Ohguri et al. | |
| 2018/0149759 A1* | 5/2018 | Sato | G01T 1/247 |

FOREIGN PATENT DOCUMENTS

| | | |
|---|---|---|
| JP | 2009-50691 A | 3/2009 |
| JP | 2010-170102 A | 8/2010 |
| JP | 2012-239657 A | 12/2012 |
| JP | 2014-55960 A | 3/2014 |
| JP | 2014-178308 A | 9/2014 |

\* cited by examiner

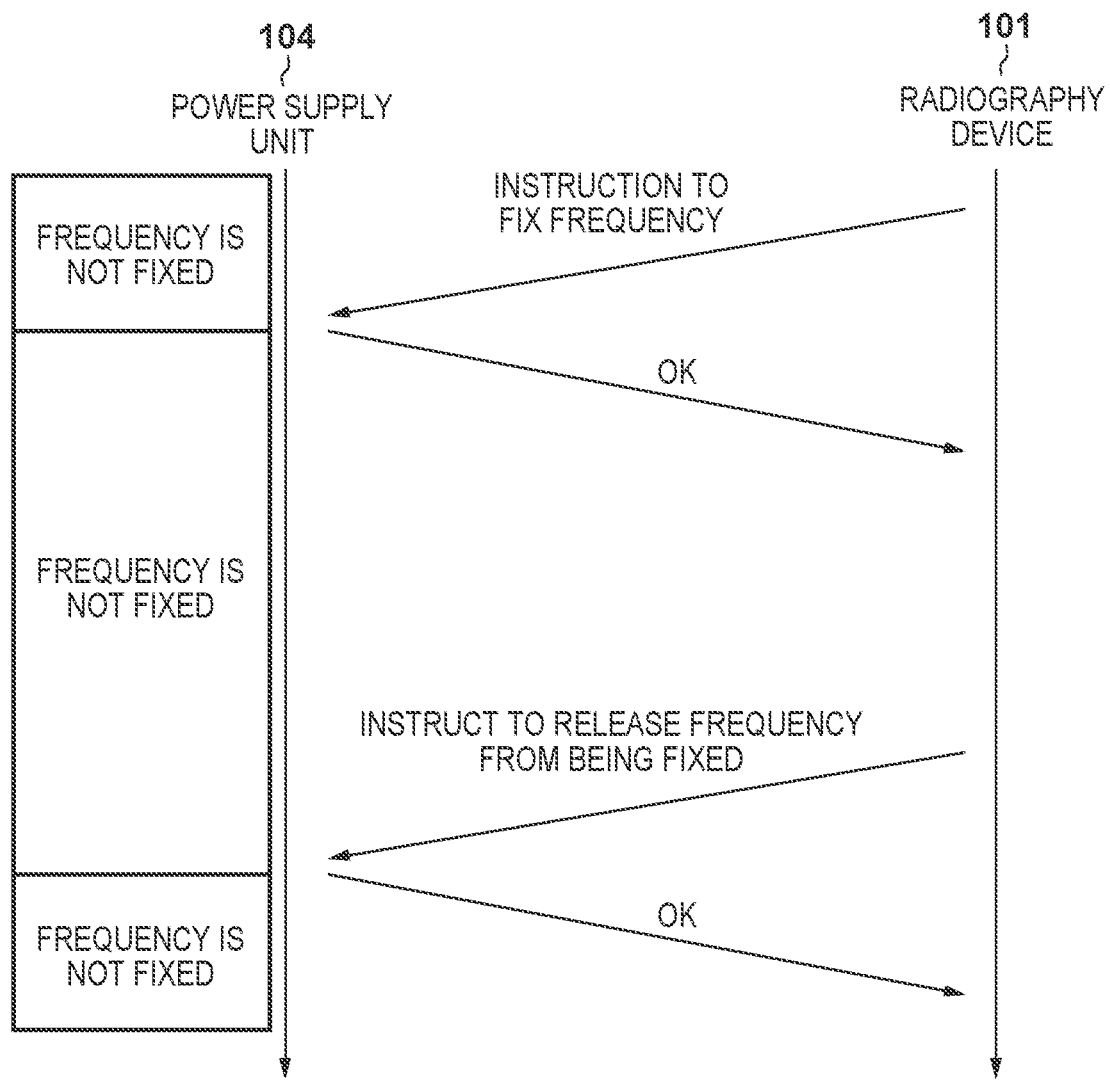

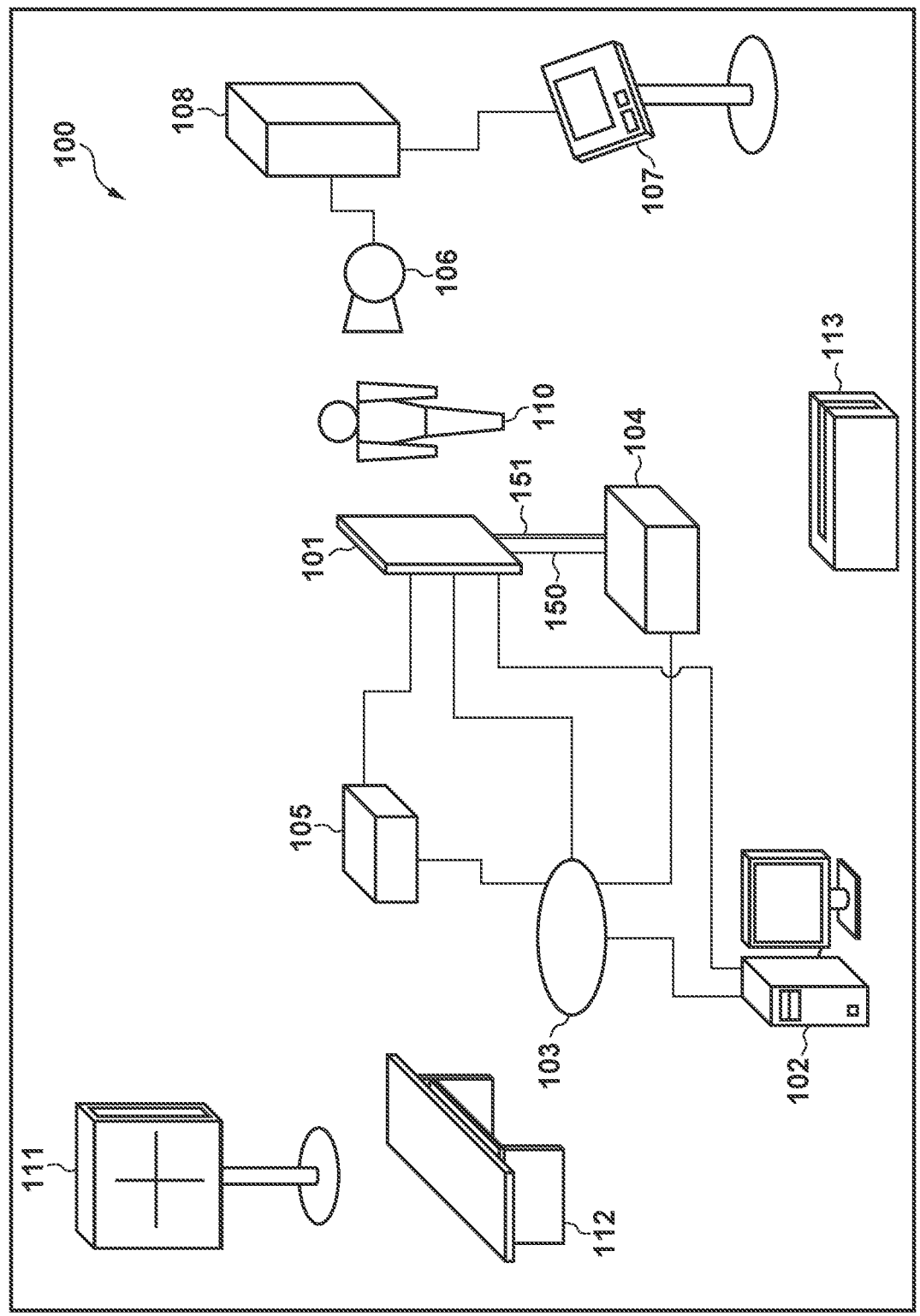

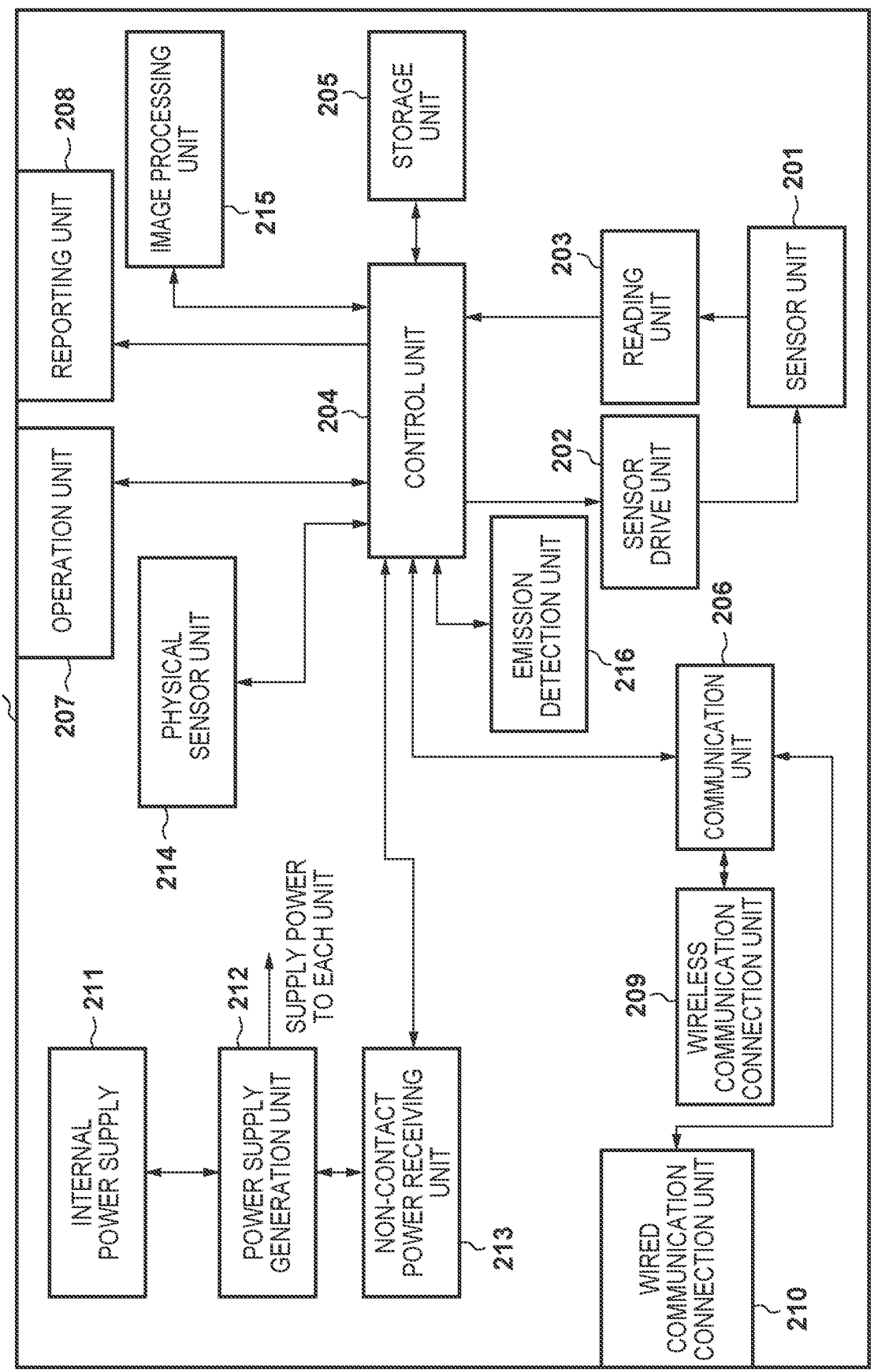

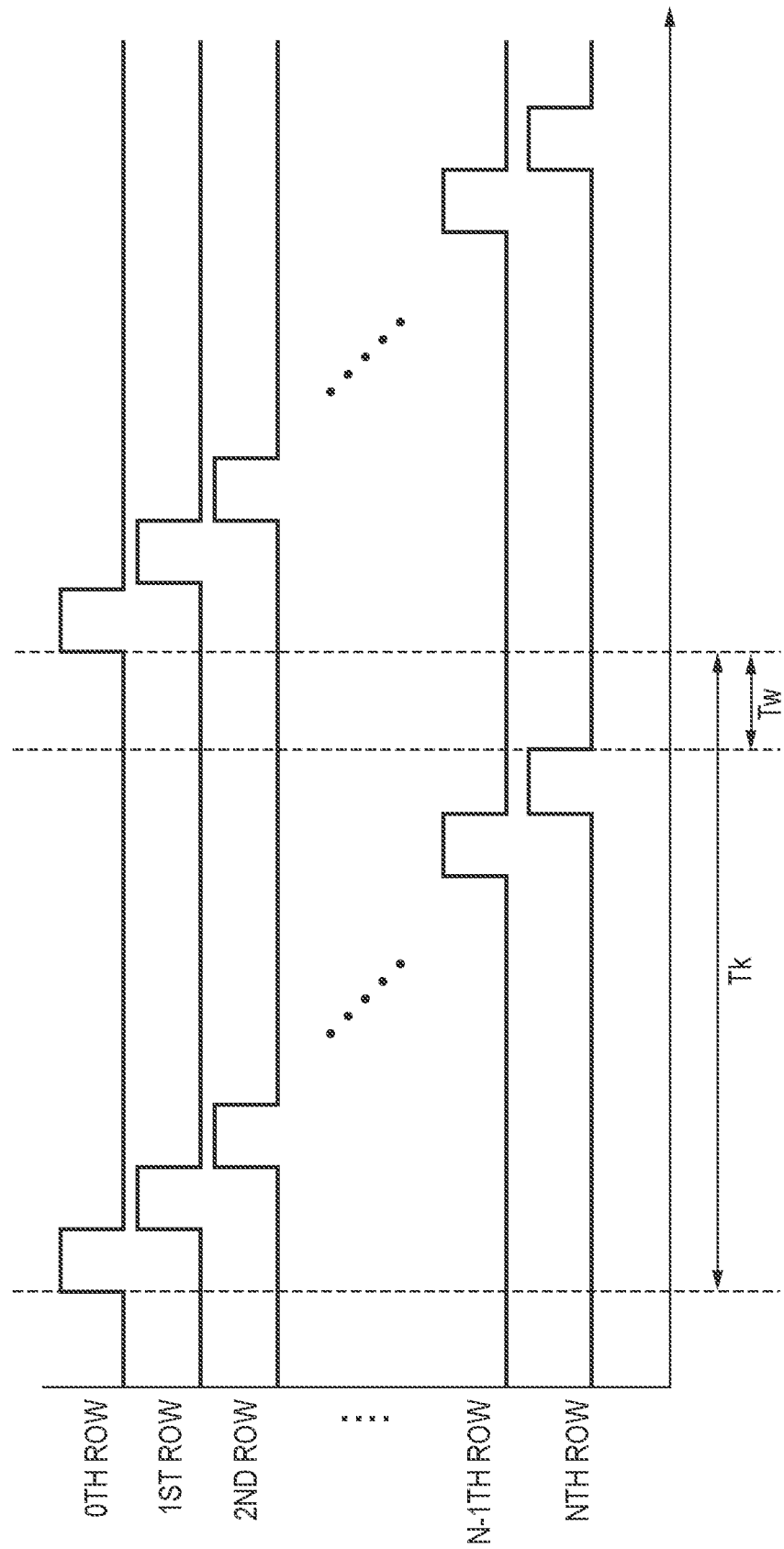

RADIOGRAPHY SYSTEM

CROSS-REFERENCE TO RELATED APPLICATIONS

This application is a Continuation of International Patent Application No. PCT/JP2020/011186, filed Mar. 13, 2020, which claims the benefit of Japanese Patent Application No. 2019-084431, filed Apr. 25, 2019, both of which are hereby incorporated by reference herein in their entirety.

BACKGROUND OF THE INVENTION

Field of the Invention

The present invention relates to a radiography system.

Background Art

Radiography systems, which use radiography devices that obtain radiographic images by detecting an intensity distribution of radiation transmitted through a subject and converting the distribution into electrical signals, are widely used. In such a radiography device, non-contact power supply is sometimes used to receive necessary power via electromagnetic field changes from the outside. If non-contact power supply is performed when reading out a signal generated by a sensor unit of the radiography device through incident radiation, changes in the electromagnetic field caused by the non-contact power supply operations may be superimposed on the signal and cause a drop in the image quality of the resulting radiographic image. Patent Document 1 describes stopping non-contact power supply from the start of image capturing until A/D conversion of radiographic image information from emitted radiation is complete.

CITATION LIST

Patent Literature

Patent Document 1: Japanese Patent Laid-Open No. 2014-55960

If the power supply is stopped during a period affected by non-contact power supply, a separate power supply unit is required, such as an internal power supply installed in the radiography device. However, when non-contact power supply is stopped, the internal power supply is no longer being charged, which may result in insufficient power when capturing a radiographic image.

An object of the present invention is to provide a technique useful for performing non-contact power supply in a radiography system.

SUMMARY OF THE INVENTION

According to some embodiments, a radiography system comprising a radiography device and a power supply device, the radiography device including a sensor unit for obtaining a radiographic image and being capable of non-contact power reception, and the power supply device being capable of non-contact power supply to the radiography device, wherein in a period in which a fluctuation in a power supply frequency of the power supply from the power supply device to the radiography device affects a signal obtained by the radiography device from the sensor unit, the power supply device supplies power to the radiography device at a constant power supply frequency, is provided.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 9 is a diagram illustrating an example of communication that specifies a power supply frequency of the radiography system illustrated in FIG. 1.

FIG. 10 is a diagram illustrating a variation on the configuration of the radiography system illustrated in FIG. 1.

FIG. 11 is a diagram illustrating an example of the configuration of a radiography device in the radiography system illustrated in FIG. 10.

FIG. 14 is a timing chart illustrating emission detection operations in the radiography system illustrated in FIG. 10.

DESCRIPTION OF THE EMBODIMENTS

Figure 1:
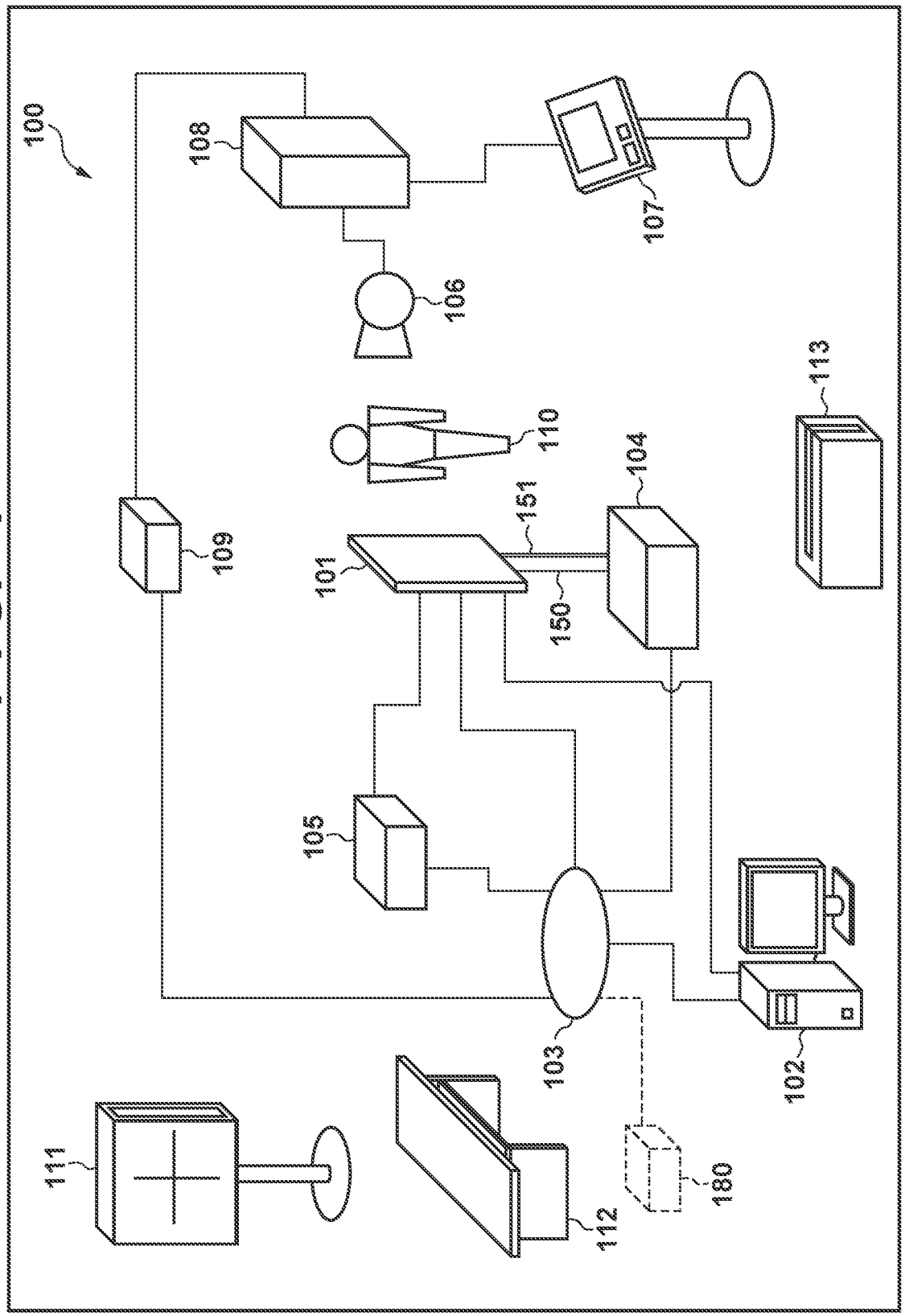
FIG. 1 is a diagram illustrating an example of the configuration of a radiography system according to an embodiment.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

In addition to α rays, β rays, γ rays, and the like, which are beams created by particles (including photons) emitted as a result of radiation decay, radiation according to the present invention can also include beams with the approximately equivalent or higher energy, such as X-rays, particle beams, cosmic rays, and the like.

A radiography system according to some embodiments of the present invention will be described with reference to FIGS. 1 to 9. FIG. 1 illustrates an example of the configuration of the radiography system 100 according to a first embodiment of the present invention. The present embodiment will describe a case where the radiography system 100 operates in a synchronous capturing mode, in which a radiography device 101 and a radiation generation device 108 capture images in synchronization. The following will first describe the constituent elements of the radiography system 100 and relationships therebetween with reference to FIG. 1.

The radiography device 101 includes a sensor unit for obtaining a radiographic image, and has a configuration that enables non-contact power reception. The radiography device 101 also has a wired or wireless communication function or both wired and wireless communication functions, and is capable of exchanging data with a console 102 over a communication path.

The console 102 is configured as a PC including a display function such as a monitor and a user input function, and is capable of conveying instructions from the user to the radiography device 101, receiving images obtained by the radiography device 101 and providing the images to the user, and the like. The console 102 also has a wired or wireless communication function, or both wired and wireless communication functions. Although the console 102 is illustrated as a stationary-type console in the configuration illustrated in FIG. 1, there are no particular restrictions on the actual operation of the radiography system 100, and thus a portable-type laptop PC, tablet device, or the like may be used as the console 102.

The radiography device 101 may send image data to the console 102 via any of a communication network 103, a power supply device 104, and an access point (AP) 105, which constitute the communication path, according to the configuration of the system. The radiography device 101 may also send image data directly to the console 102. The communication network 103 is, for example, a LAN network, and by connecting the radiography device 101 and the console 102 to the communication network 103 using a hard-wire cable, data can be exchanged therebetween.

The radiography device 101 has a function that enables power to be received in a non-contact manner, and by placing the radiography device 101 in close proximity to the power supply device 104, which can supply power to the radiography device 101, the power supply device 104 can supply power to the radiography device 101 in a non-contact manner. Furthermore, if the radiography device 101 and the power supply device 104 are provided with a non-contact proximity communication function, a configuration for communication may be provided in parts near a non-contact power receiving unit of the radiography device 101 and a non-contact power supply unit of the power supply device 104. This makes it possible for the radiography device 101 to receive power and communicate through the power supply device 104 by placing the radiography device 101 and the power supply device 104 in close proximity.

In the configuration illustrated in FIG. 1, of lines connecting the radiography device 101 and the power supply device 104, a line 150 indicates a connection for communication (wired and/or wireless) and a line 151 indicates a connection for power supply (non-contact power supply). In the configuration illustrated in FIG. 1, the power supply device 104 is shown as being connected to the console 102 via the communication network 103, but the configuration is not limited thereto. The configuration may be such that the power supply device 104 and the console 102 are electrically connected to each other directly.

If the radiography device 101 is provided with a wireless communication function, the radiography device 101 may exchange data with the console 102 via the AP 105. Additionally, in the configuration illustrated in FIG. 1, the AP 105 is shown as being connected to the console 102 via the communication network 103, but the AP 105 may be electrically connected to the console 102 directly, in the same manner as the power supply device 104 described above.

Furthermore, if the radiography device 101, the console 102, the power supply device 104, and the AP 105 are provided with a function for exchanging data directly with each other, these elements may exchange data with each other directly, wirelessly or over wires.

The foregoing has been a description of an example of paths used to exchange data between the radiography device 101 and the console 102.

A cradle 113, which is a charger of the radiography device 101, will be described here. Although the internal configuration of the radiography device 101 will be described later, the radiography device 101 includes an internal power supply such as a battery, and the internal power supply can be charged by supplying power to the radiography device 101 from outside. It is possible to charge the internal power supply by receiving power from the aforementioned power supply device 104, but the cradle 113 may be provided in the radiography system 100 as a device capable of charging when the radiography device 101 is mounted thereon, such as when radiographic images are not being captured.

A mechanism for supplying power from the cradle 113 to the radiography device 101 may be a mechanism that requires electrical contact, or may be a non-contact power supply mechanism. When the radiography device 101 is mounted on the cradle 113, the cradle 113 detects the radiography device 101 and enters a state in which the supply of power can start. This makes it possible for the radiography device 101 to receive power and charge the internal power supply.

The configuration illustrated in FIG. 1 is an example in which the cradle 113 is provided independently, without communicating with other constituent elements of the radiography system 100, but the configuration is not limited thereto. A plurality of cradles 113 may have communication functions, and may be connected to other constituent elements of the radiography system 100 via the communication network 103 or the like. For example, while the radiography device 101 is mounted on the cradle 113, communication between the radiography device 101 and constituent elements such as the console 102 may be possible via the cradle 113.

An overview of capturing an image of a subject 110 using radiation will be described next. The radiography device 101 is installed in a position where radiation emitted from a radiation tube 106 and transmitted through the subject 110 is received in order to capture an image of the subject 110.

To give an example of the flow of image capturing, after the radiography device 101 is started up by a user such as a radiographer, the console 102 is operated by the user to put the radiography device 101 into a state in which an image can be captured. The user then operates a radiation generation device console 107 to set image capturing conditions (tube voltage, tube current, emission time, and the like of the radiation tube 106) under which the radiation is to be emitted. After the above processing is complete, the user confirms that preparations for capturing the image, including the subject 110, are complete, and presses a radiation exposure switch on the radiation generation device console 107 to expose the subject with radiation.

At the time of radiation exposure, the radiation generation device 108 notifies the radiography device 101 of a signal indicating that radiation is about to be emitted, via a connecter 109, the communication network 103, and the like. In the configuration illustrated in FIG. 1, the radiography device 101 and the radiation generation device 108 are connected via the connecter 109 and the communication network 103, but the configuration is not limited thereto, and these devices may be connected directly as described above.

When the signal indicating that radiation is about to be emitted arrives at the radiography device 101, the radiography device 101 confirms whether or not preparations for emitting radiation are complete, and if there is no problem, permission for emission is returned to the radiation generation device 108. The radiation is emitted in this manner.

Upon detecting the end of radiation emission through various methods, such as through a notification from the radiation generation device 108 or by referring to a predetermined set time, the radiography device 101 starts generating image data of a radiographic image. The generated image data is sent to the console 102 through the aforementioned communication path. The image data sent to the console 102 can, for example, be displayed as a radiation image in a display unit included in the console 102.

The radiography device 101 may be incorporated into a frame 111, a bed 112, or the like for capturing images, in accordance with conditions such as the area to be captured, the state of the subject, and so on.

The foregoing has described operations in the synchronous capturing mode, in which the radiography device 101 and the radiation generation device 108 capture an image in synchronization.

Figure 2:
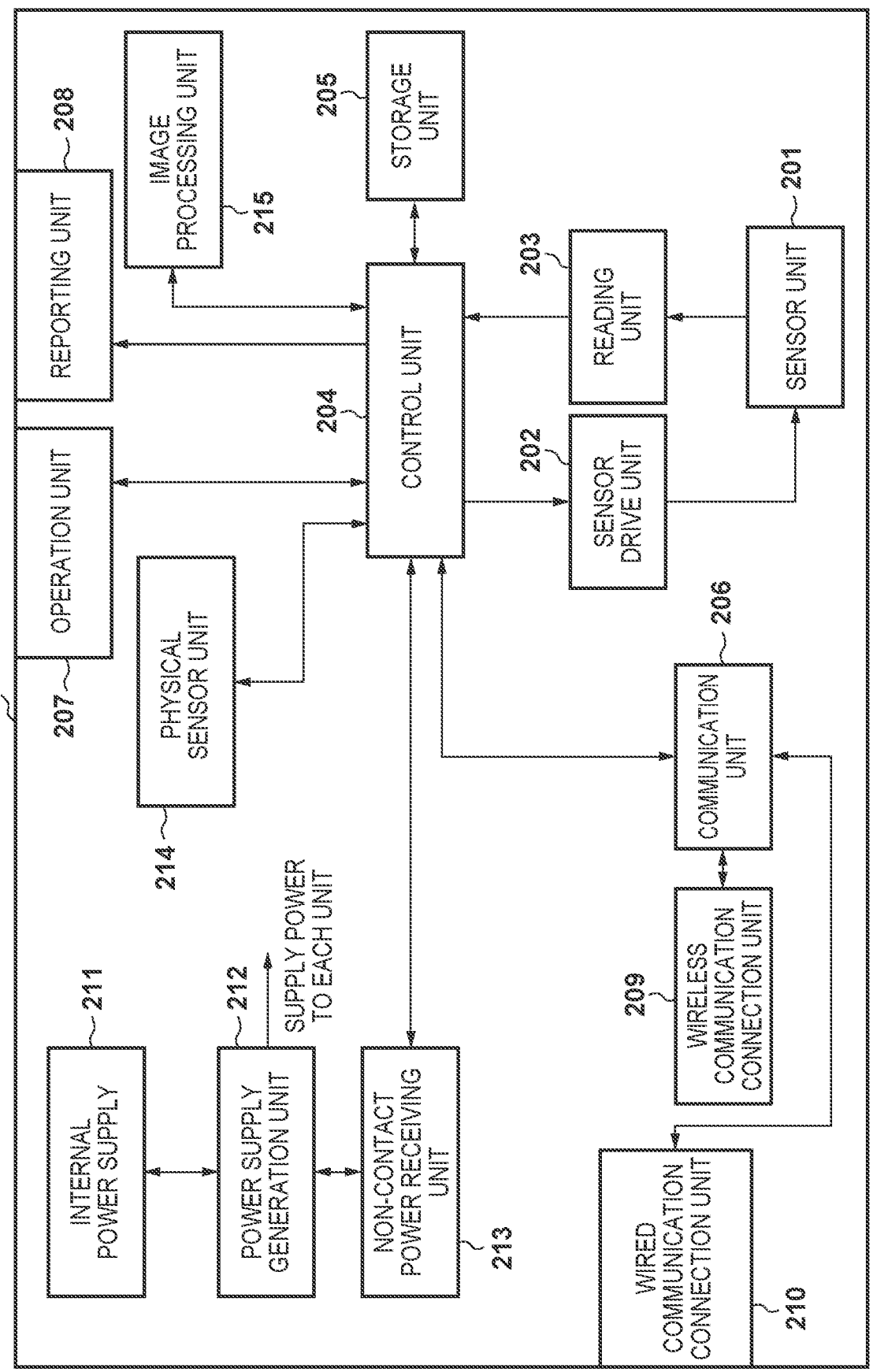
FIG. 2 is a diagram illustrating an example of the configuration of a radiography device in the radiography system illustrated in FIG. 1.

The radiography device 101 will be described next with reference to FIG. 2. FIG. 2 is a diagram illustrating an example of the configuration of the radiography device 101. The radiography device 101 includes a sensor unit 201 that converts incident radiation into electrical signals in order to obtain a radiographic image. The sensor unit 201 can be configured including, for example, a scintillator that converts radiation into light and an array of photodetectors that detect the light converted by the scintillator. The scintillator and the photodetector array each have a two-dimensional planar shape, and can be adjacent to each other with their faces opposite each other. The scintillator is excited by the radiation and emits visible light, and an electrical charge corresponding to the intensity and duration of the light is accumulated in each of pixels in the photodetector array.

A sensor drive unit 202 drives the sensor unit 201, which detects radiation as an electrical charge. A reading unit 203 receives the electrical charge output as a result of driving the sensor unit 201 and converts the electrical charge into digital information. When extracting the accumulated electrical charge, the sensor drive unit 202 selects a photodetector, among the photodetector array in the sensor unit 201, from which a signal is to be extracted. The reading unit 203 amplifies and then digitizes the signal charge extracted from the photodetector selected by the sensor drive unit 202.

The reading unit 203 sends the digitized image data to a control unit 204, and the control unit 204 then sends the image data to a storage unit 205. The image data stored in the storage unit 205 may be immediately sent to an external device via a communication unit 206. The image data may also be sent to the external device via the communication unit 206 after some kind of processing is performed by the control unit 204. The image data may also be stored in the storage unit 205.

The control unit 204 performs processing related to the control of each constituent element of the radiography device 101. For example, with respect to capturing an image, the control unit 204 outputs an instruction to the sensor drive unit 202 for driving the sensor unit 201. The control unit 204 may perform driving to save the obtained image data into the storage unit 205, or the image data saved in the storage unit 205 may be retrieved from the storage unit 205 and the image data may be sent to the external device via the communication unit 206.

The control unit 204 also transmits the image data to other devices via the communication unit 206, and receives instructions from the console 102 and the like via the communication unit 206. The control unit 204 also switches the radiography device 101 on and off in response to an operation made by the user through an operation unit 207. Furthermore, the control unit 204 can also notify the user of operation statuses, error states, and the like via a reporting unit 208.

In the present embodiment, the content of the processing described above is handled by the one control unit 204, but the radiography device 101 may include a plurality of control units 204 for respective ones of predetermined functions, and the processing may be shared by those control units 204. The control unit 204 can be realized by various configurations such as a CPU, an MPU, a FPGA, a CPLD, and the like, and the specific implementation is not particularly limited. An appropriate configuration can be selected according to the functions, performance, and so on required of the radiography device 101.

The storage unit 205 can be used to save image data obtained by the radiography device 101, log information indicating results of internal processing, and the like. If the control unit 204 is a device that uses software, such as a CPU, the storage unit 205 can also store software and the like for the control unit. The specific implementation of the storage unit 205 is not particularly limited, and the storage unit 205 can be provided with various types of memory, an HDD, various combinations of volatile/non-volatile, and so on. Although only one storage unit 205 is illustrated in the configuration in FIG. 2, the radiography device 101 may be provided with a plurality of storage units 205.

The communication unit 206 performs processing for implementing communication between the radiography device 101 and other devices constituting the radiography system 100. The communication unit 206 in the present embodiment is connected to a wireless communication connection unit 209 for wireless communication, and can communicate with the console 102, the AP 105, and the like via the wireless communication connection unit 209. An antenna for wireless communication can be given as an example of the wireless communication connection unit 209. The communication unit 206 is also connected to a wired communication connection unit 210, and can communicate with the console 102 and the like via the wired communication connection unit 210. In the configuration illustrated in FIG. 2, the wired communication connection unit 210 is provided so as to be in contact with an exterior of the radiography device 101, and may be connected via a connector, for example. The wired communication connection unit 210 may also have a function for short-range non-contact communication. The present embodiment will also describe elements such as the power supply device 104, which will be described later, as having functions for short-range non-contact communication, for example. The communication unit 206 is not limited to the form described above, and may be configured so as to be capable of only wired communication or wireless communication. The standard, method of communication, and the like are not particularly limited as well.

The radiography device 101 includes an internal power supply 211. In the present embodiment, the internal power supply 211 is a rechargeable battery, and can be removed from the radiography device 101. The internal power supply 211 is not limited to this example, and can be rechargeable, non-rechargeable, removable, or non-removable, and can also employ various combinations of power generation methods.

A power supply generation unit 212 generates, distributes, and supplies voltage and current required by each constituent element of the radiography device 101 from the power provided by the internal power supply 211. When the radiography device 101 is in near the non-contact power supply function of the power supply device 104, the power supplied from the power supply device 104 can be received using a non-contact power receiving unit 213. Using the received power, the power supply generation unit 212 supplies power to the respective constituent elements of the radiography device 101, charges the internal power supply 211, and the like. The non-contact power receiving unit 213 can start non-contact power reception by approaching the power supply device 104 that performs the non-contact power supply. As described above, the non-contact power receiving unit 213 may not only receive power, but also exchange information pertaining to the non-contact power supply with the power supply side (the power supply device 104) using a power receiving mechanism, communication functions incorporated into components and units constituting the power receiving mechanism, and the like.

In the present embodiment, the non-contact power receiving unit 213 can communicate with the power supply device 104 using the same components for receiving power (e.g., a coil and the like). Accordingly, in the configuration illustrated in FIG. 2, the non-contact power receiving unit 213 is connected not only to the power supply generation unit 212, but also to the control unit 204. The communication between the non-contact power receiving unit 213 and the control unit 204 is not limited thereto, however, and the communication between the non-contact power receiving unit 213 and the control unit 204 may be performed via the communication unit 206 or another constituent element.

The operation unit 207 is used for accepting operations from the user to the radiography device 101. The method of implementing the operation unit 207 is not particularly limited, and any method is acceptable as long as inputs can be accepted from the user. For example, the operation unit 207 can be realized by various types of switches, a touch panel, and the like that are manually operated by the user. The operation unit 207 may include a receiving unit that accepts inputs from a remote controller that enables the user to operate the radiography device 101 away from the radiography device 101.

The reporting unit 208 is used to report the status or the like of the radiography device 101 to the user and the like. The method of implementation is not particularly limited, and can be realized by a lamp display using an LED or the like, a monitor display using an LCD or the like, and so on. As one method of notifying the user, the reporting unit 208 may include an audio output function such as a speaker.

A physical sensor unit 214 is a sensor unit for detecting various physical events. Examples of physical phenomena include temperature, acceleration, geomagnetism, electromagnetic fields, and the like. On the basis of detected information about physical events, the control unit 204 may determine the status of the radiography device 101 and issue a warning via the reporting unit 208 when the system is subjected to high temperatures, a strong impact, or the like. Additionally, on the basis of detected information about physical events, the control unit 204 determines the installation orientation of the radiography device 101 and the like, and then transmits information for improving usability to the user or the console 102 (e.g., to inform the user of an abnormal insertion direction into the frame 111).

An image processing unit 215 performs image correction processing, such as offset correction and gain correction, on the image data converted to digital values by the reading unit 203 or the image data stored in the storage unit 205. Offset correction removes an offset component produced by dark current, regardless of radiation emission, by calculating a difference between image data obtained in a state where radiation is emitted and image data obtained in a state where no radiation is emitted. Gain correction is performed by dividing the obtained image data by image data captured by emitting radiation for all pixels uniformly or the like in order to correct for the variation in the gain of each pixel (photodetector). Generally, more advanced image processing is performed after the image data is transferred to the console 102 or the like, but the configuration is not limited thereto, and the details of the image processing performed inside the radiography device 101 are not limited.

Figure 3:
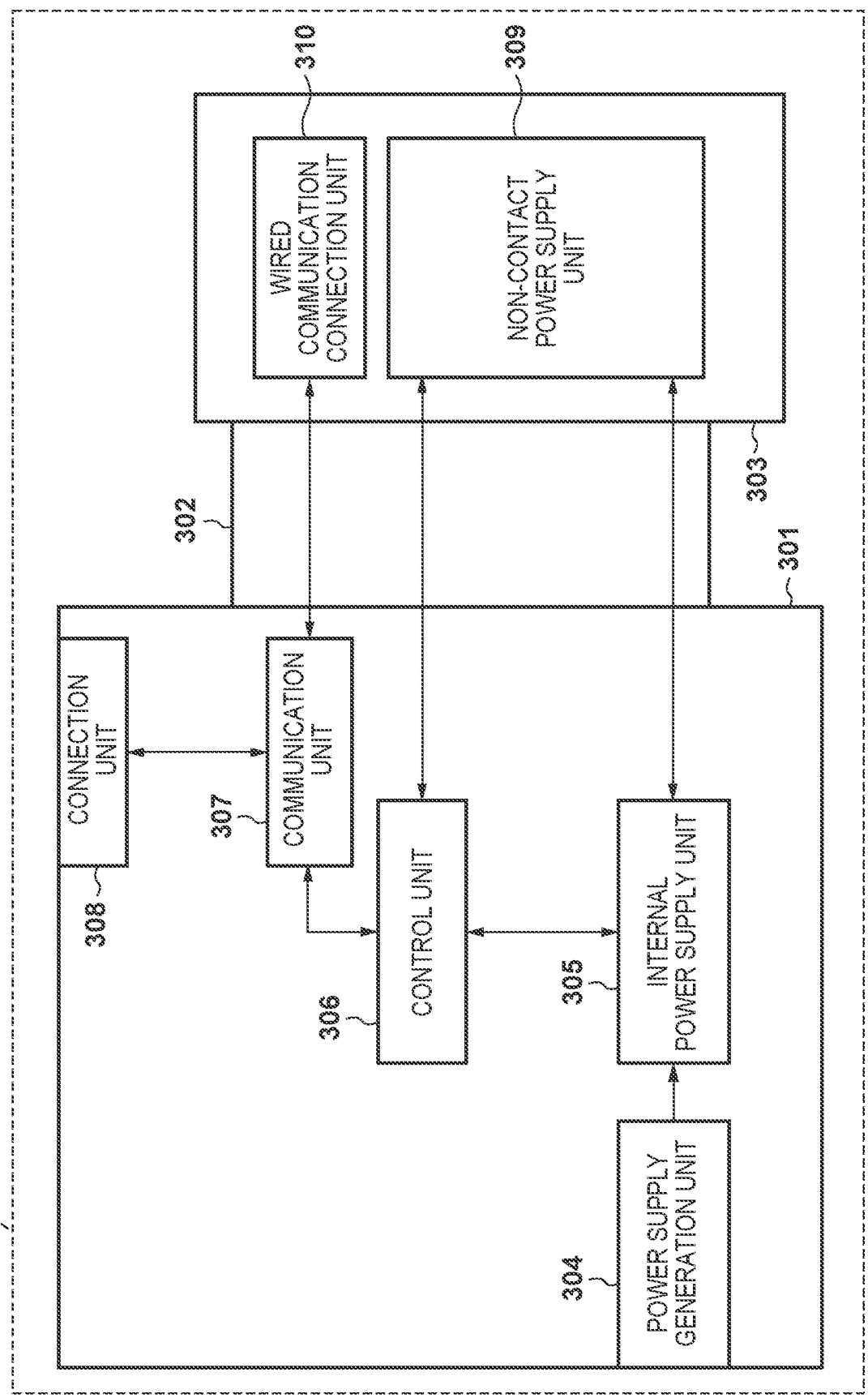
FIG. 3 is a diagram illustrating an example of the configuration of a power supply device in the radiography system illustrated in FIG. 1.

The configuration of the power supply device 104 will be described next. FIG. 3 illustrates an example of the configuration of the power supply device 104. The power supply device 104 according to the present embodiment includes a main power supply unit body 301, a power supply unit cable 302, and a power supply unit proximity unit 303.

When supplying power to the radiography device 101, the power supply unit proximity unit 303 is brought into proximity or contact with the non-contact power receiving unit 213 of the radiography device 101. The main power supply unit body 301 can be disposed at a distance from the radiography device 101 via the power supply unit cable 302. Here, the term "contact" is intended to refer to contact between the exteriors of the radiography device 101 and the power supply device 104.

The main power supply unit body 301 includes a power supply generation unit 304 that receives power from an AC power source and converts the power to a DC voltage, and an internal power supply unit 305 that generates the power used by the constituent elements of the power supply device 104. The main power supply unit body 301 includes a control unit 306 that controls the constituent elements of the power supply device 104, a communication unit 307 that communicates with the power supply device 104 and other components of the radiography system 100, and a connection unit 308 for communicating with entities aside from the radiography device 101.

The power supply unit proximity unit 303 includes a non-contact power supply unit 309 and a wired communication connection unit 310. The non-contact power supply unit 309 receives power for power supply from the internal power supply unit 305, and the power supply is controlled by the control unit 306. Like the non-contact power receiving unit 213 of the radiography device 101, in the present embodiment, communication pertaining to the non-contact power supply is performed using the same components that are used to supply power (e.g., coils).

The wired communication connection unit 310 is a counterpart to the wired communication connection unit 210 of the aforementioned radiography device 101. As described above, the wired communication connection unit 210 according to the present embodiment assumes short-range wireless communication, and thus the wired communication connection unit 310 of the corresponding power supply device 104 can also have the same configuration and functions as the wired communication connection unit 210. However, the part related to communication may be implemented by a connection which makes contact, such as a connector. The wired communication connection unit 310 is connected to the communication unit 307 via the power supply unit cable 302 in order to perform communication.

The present embodiment describes a case where the main power supply unit body 301 and the power supply unit proximity unit 303 are disposed at a distance via the power supply unit cable 302, but the configuration is not limited thereto. The power supply unit proximity unit 303 may be incorporated into the main power supply unit body 301.

Figure 4:
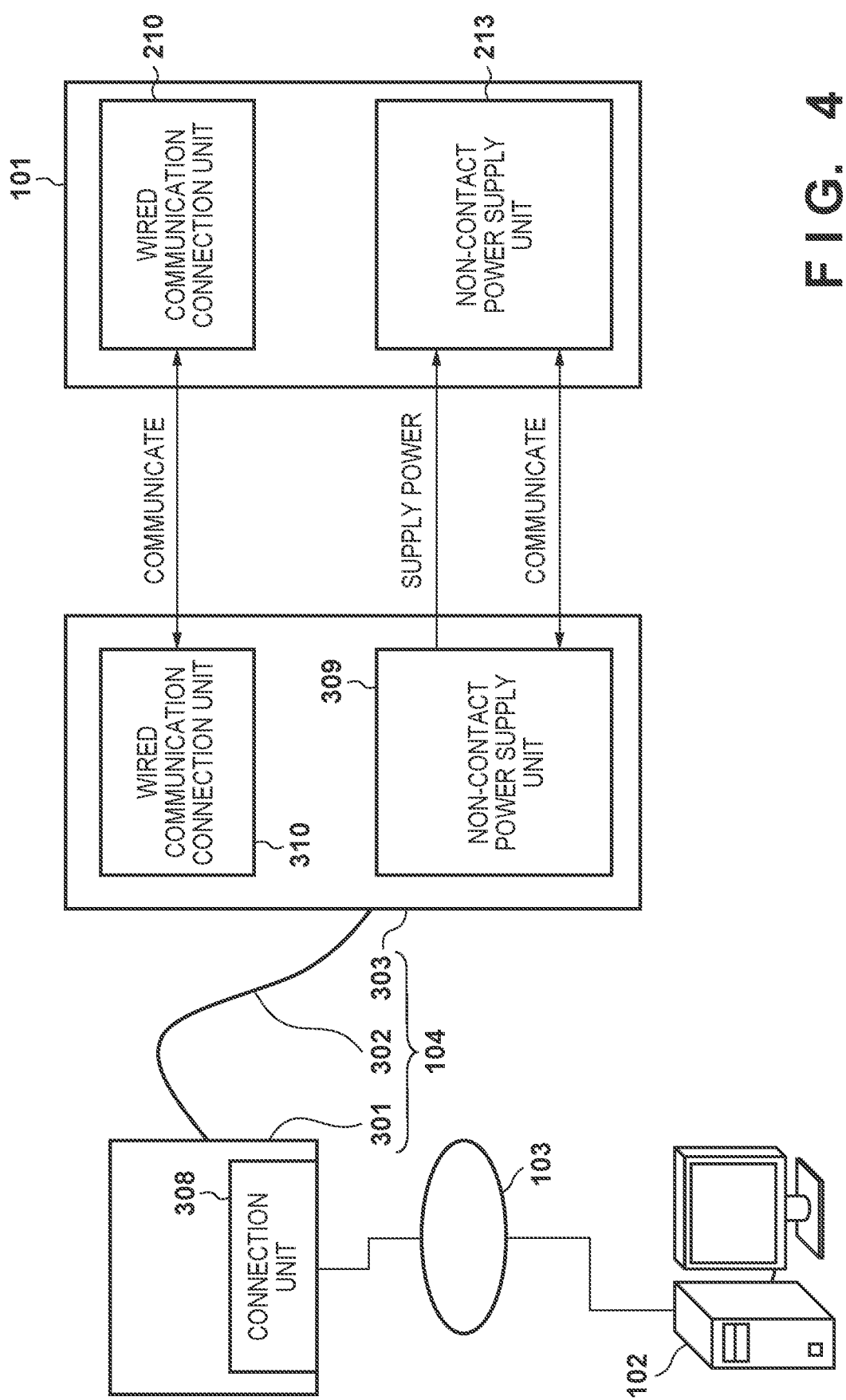
FIG. 4 is a diagram illustrating an example of communication and power supply between the radiography device and the power supply device in the radiography system illustrated in FIG. 1.

FIG. 4 illustrates an example of the connection between the radiography device 101 and the power supply device 104. FIG. 4 illustrates an example of how the radiography device 101 is connected to the console 102, and what kind of information is exchanged. FIG. 4 focuses on parts related to the non-contact power supply between the radiography device 101 and the power supply device 104, the wired connection communication, and the proximity non-contact communication, and as such, the communication path and types of connections made by other wireless connections will not be described. Power transmission and information transfer are also illustrated in FIG. 4.

When the radiography device 101 receives power from the power supply device 104, the power supply unit proximity unit 303 is brought near the radiography device 101 in advance. To stabilize the placement, the exteriors of housings of the radiography device 101 and the power supply device 104 may be in contact with each other. Upon entering this state, communication for mutual recognition between the non-contact power supply unit 309 and the non-contact power receiving unit 213 takes place via those units' respective power supply/power reception coils. When it is determined that power can be transmitted between the radiography device 101 and the power supply device 104, the power supply device 104 supplies power to the radiography device 101 via the non-contact power supply unit 309. The radiography device 101 receives power via the non-contact power receiving unit 213 and uses the power within the radiography device 101.

When transferring image data obtained by the radiography device 101 to an external device, the image data is exchanged using the wired communication connection units 210 and 310. For example, when the radiography device 101 transfers obtained image data to the console 102, the image data is sent from the radiography device 101 to the console 102 via the wired communication connection units 210 and 310, the communication unit 307, the connection unit 308, and the communication network 103.

As has been mentioned repeatedly thus far, each connection is merely an example. Accordingly, for example, the wired communication connection units 210 and 310 may employ methods which use contact via connectors, and communication pertaining to the non-contact power supply may be realized using a different path. Furthermore, the image data is not limited to being sent from the radiography device 101 to the console 102 via the power supply device 104, and may instead be sent directly from the radiography device 101 to the console 102.

Figure 5:
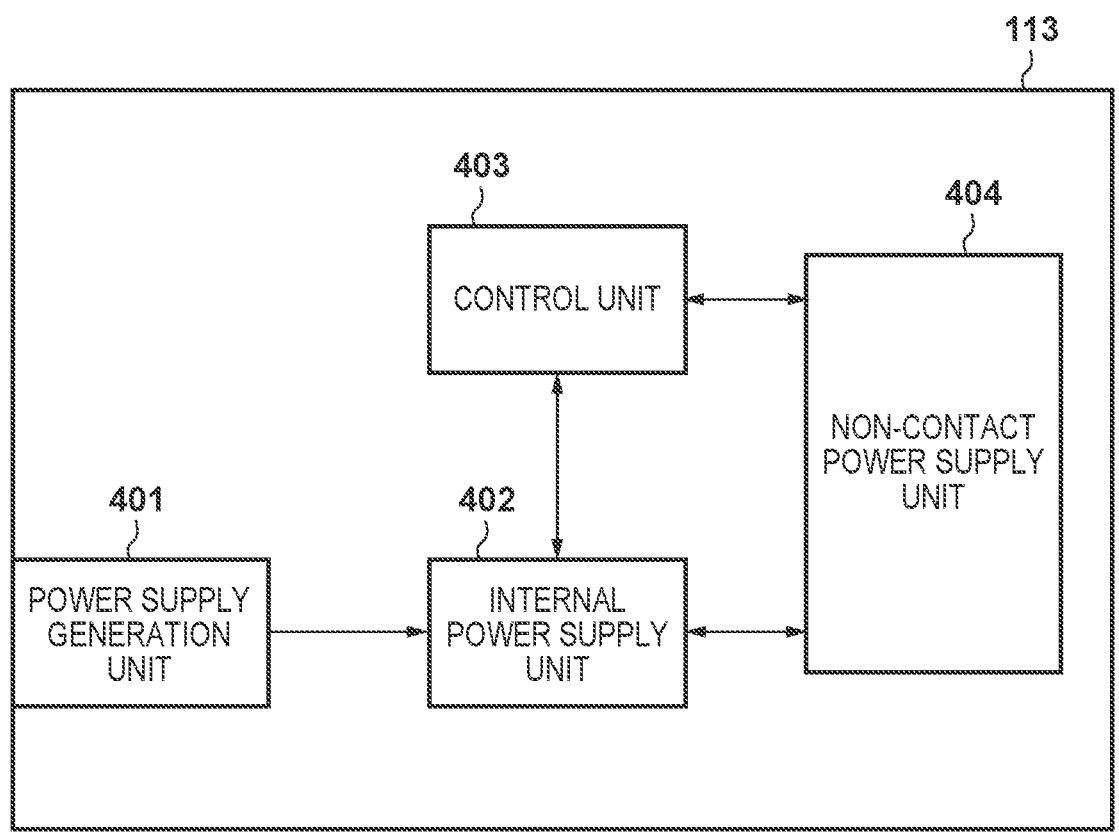
FIG. 5 is a diagram illustrating an example of the configuration of a cradle in the radiography system illustrated in FIG. 1.

An example of the configuration of the cradle 113 will be described next with reference to FIG. 5. As described above, the cradle 113 is used when charging the radiography device 101. Accordingly, the cradle 113 includes a power supply generation unit 401 that receives power from an AC power source and converts the power to DC voltage, an internal power supply unit 402 that generates power used by the constituent elements in the cradle 113, a control unit 403 that controls the interior of the cradle 113, and a non-contact power supply unit 404.

The general processing performed when supplying power from the cradle 113 to the radiography device 101 is the same as that performed in the power supply device 104 described above, and will therefore not be described here. Additionally, as described above, the cradle 113 may be provided with a mechanism that enables the radiography device 101 to communicate with the other constituent elements of the radiography system 100 when the cradle 113 and the radiography device 101 are connected.

The power supply unit proximity unit 303 of the power supply device 104 may be provided in a location of the frame 111, the bed 112, or the like into which the radiography device 101 fits in advance. In this case, a plurality of the power supply unit proximity units 303 may be provided for a single main power supply unit body 301 of the power supply device 104, and a plurality of the power supply devices 104 may be provided in the radiography system 100. Providing the power supply unit proximity unit 303 in the frame 111, the bed 112, or the like makes it possible to perform non-contact power supply to the radiography device 101 when the radiography device 101 is mounted on the frame 111, the bed 112, or the like, in the same manner as when connected to the power supply device 104. For example, the full configuration of the power supply device 104 may be incorporated into the frame 111. Additionally, with respect to the shape of the power supply device 104, the power supply unit proximity unit 303 and the main power supply unit body 301 may be connected by the power supply unit cable 302 as illustrated in FIG. 3, or the power supply unit proximity unit 303 and the main power supply unit body 301 may be an integrated entity.

Figure 6:
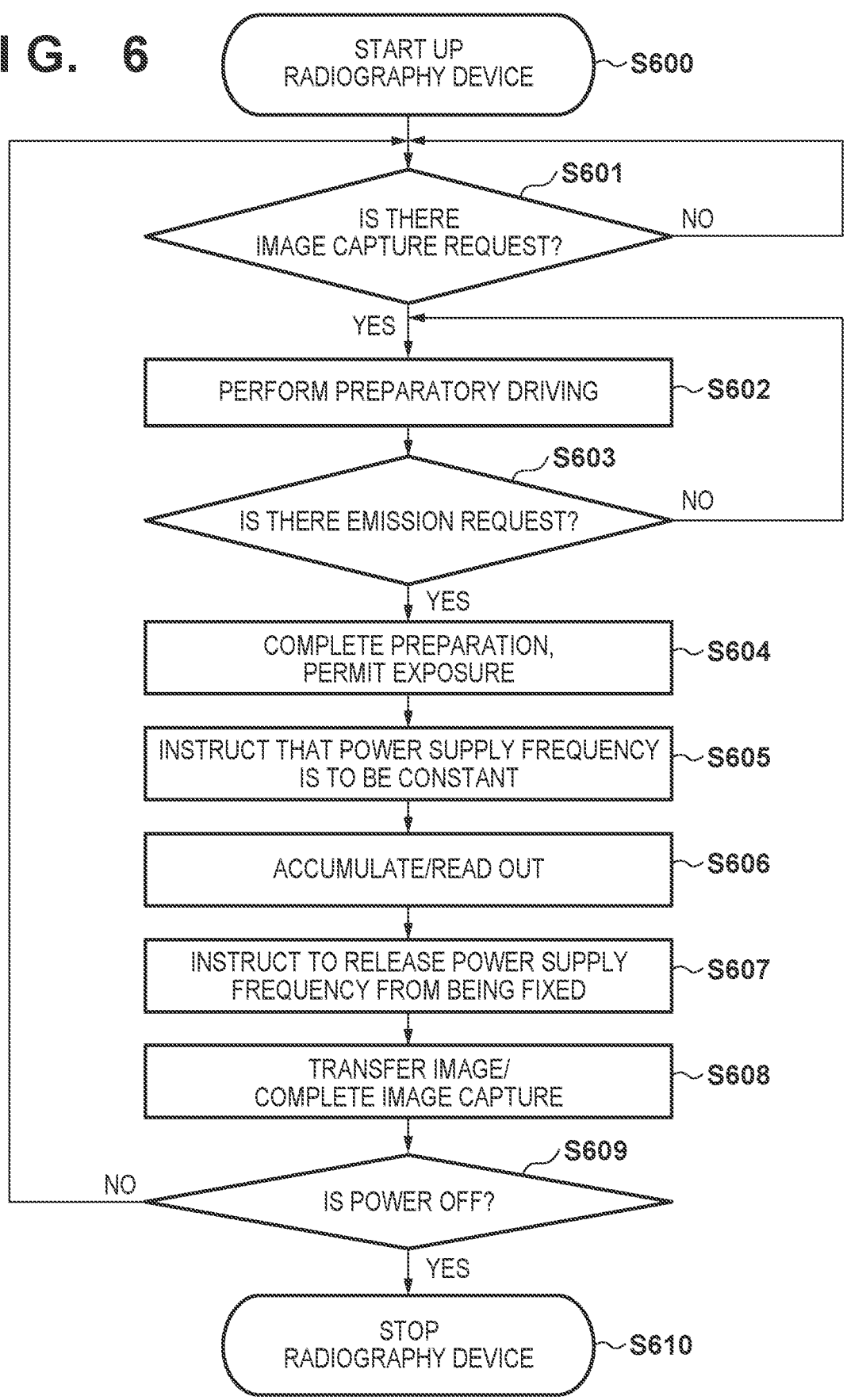
FIG. 6 is a flowchart illustrating processing performed when capturing an image in the radiography system illustrated in FIG. 1.
Figure 7:
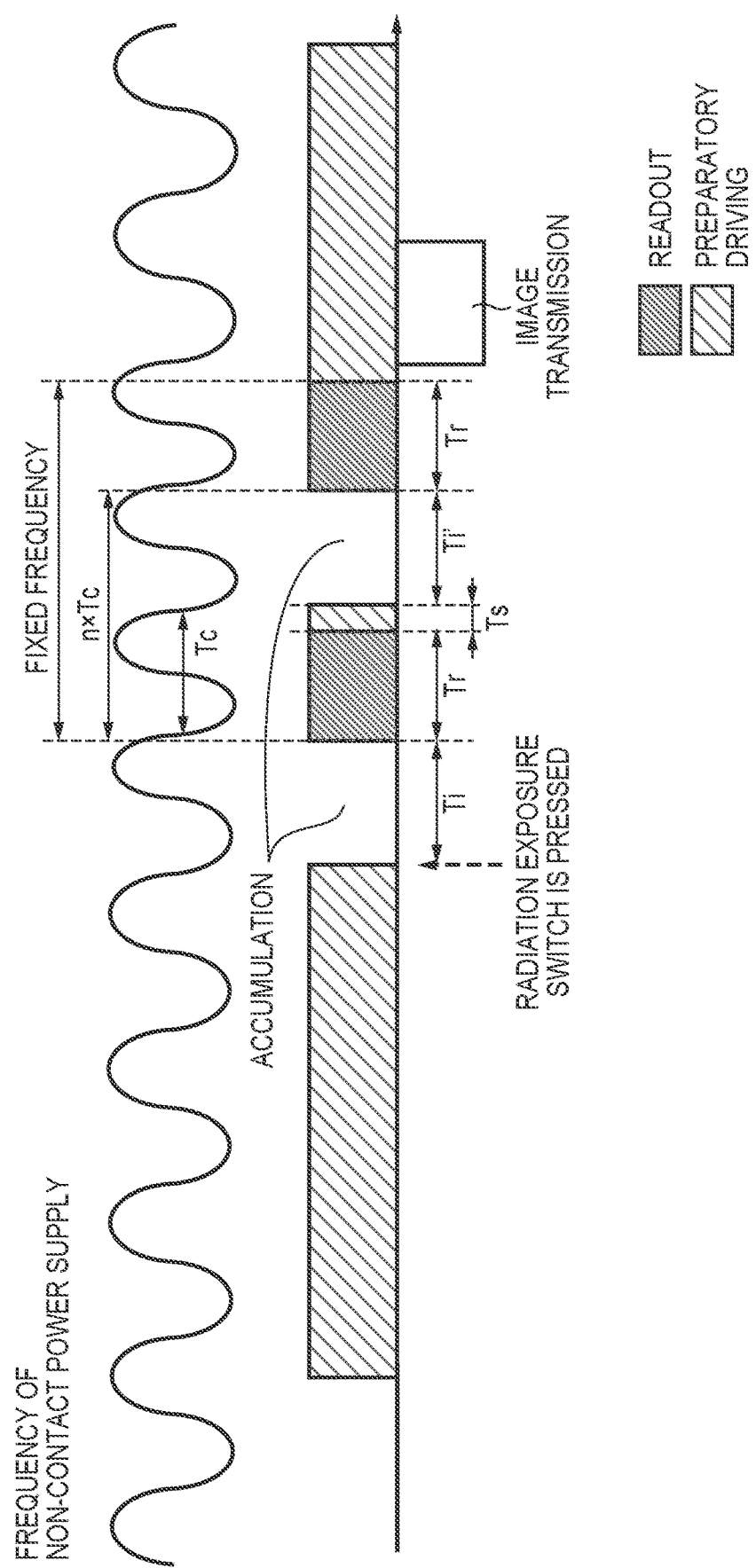
FIG. 7 is a timing chart illustrating operations performed when capturing an image in the radiography system illustrated in FIG. 1.

Operations of the radiography system 100 when performing non-contact power supply along with capturing a radiographic image in the synchronous capturing mode will be described next. Although details will be given later, in the present embodiment, while non-contact power supply is performed from the power supply device 104 to the radiography device 101, the frequency of the non-contact power supply is controlled so as not to vary during a readout period of the image data of the radiography device 101. FIGS. 6 and 7 are a flowchart and a timing chart, respectively, illustrating processing performed by the radiography system 100 when capturing an image in the synchronous capturing mode.

When the radiography device 101 is started up by the user, power is supplied from the power supply generation unit 212 to the necessary constituent elements, and the radiography device 101 starts up (S600). Here, the descriptions will assume that the constituent elements of the radiography system 100 which are necessary for image capture are started as well. For example, at the point in time of S600, the power supply device 104 is in a state in which power can be supplied to the radiography device 101. A trigger for starting up the device may be a detection of the user's intention to start up the device via operation of the operation unit 207 or via the physical sensor unit 214, the removable internal power supply 211 being attached, the power supply unit proximity unit 303 of the power supply device 104 being connected to the radiography device 101, or the like. At this time, it is not necessary to start up all the constituent elements in the radiography device 101. For example, the constituent elements used in image capturing, such as the sensor unit 201, need not be started up until a request to capture an image is made. Additionally, the radiography device 101 may be started up in response to the start of power supply to the radiography device 101 from the exterior, either contact or non-contact. The present embodiment assumes that non-contact power supply is performed continuously from when the radiography device is started up in S600 of FIG. 6 to when the radiography device stops in S610.

When the radiography device 101 starts up, the sequence moves to S601, where the control unit 204 of the radiography device 101 determines whether or not there is an image capture request from the radiation generation device 108. If there is no request, the device continues to stand by for an image capture request. If there is an image capture request, the sequence moves to S602.

In S602, the radiography device 101 performs image capture preparation operations. As the image capture preparation operations, the radiography device 101 supplies power from the power supply generation unit 212 to the sensor unit 201 and starts up the sensor unit 201. After this, the control unit 204 sends an instruction to start preparatory driving to the sensor drive unit 202, in response to which the sensor drive unit 202 performs preparatory driving for the sensor unit 201. The preparatory driving is an operation (a reset operation) in which charges are continuously read out while scanning the sensor array in the row direction in order to discharge charges accumulated in the sensor unit 201 due to dark current.

If the user presses the radiation exposure switch of the radiation generation device console 107 while the preparatory driving is underway, communication is performed between the radiation generation device 108 and the radiography device 101 via the connecter 109, the communication network 103, and the like. Specifically, the radiation generation device 108 sends a request for exposure to the radiography device 101, and when the radiography device 101 receives that request (YES in S603), the sequence moves to S604. In S604, the radiography device 101 shifts the sensor unit 201 to a state in which charges can be accumulated in response to radiation and sends, to the radiation generation device 108, a response that an image can be captured or that exposure is permitted, after which radiation is emitted. The above-described preparatory driving is performed while the user is not pressing the radiation exposure switch (NO in S603).

Once the permission for exposure is sent in S604, the control unit 204 sends, to the power supply device 104 that performs non-contact power supply to the radiography device 101, a signal instructing that the power supply frequency of the non-contact power supply is to have a constant frequency that does not fluctuate (S605). As described above, in the present embodiment, the non-contact power receiving unit 213 and the non-contact power supply unit 309 have communication functions which enable the exchange of information pertaining to the supply of power. Accordingly, the control unit 204 of the radiography device 101 can issue instructions pertaining to the power supply frequency of the power supply via the non-contact power receiving unit 213. The instruction sent from the non-contact power receiving unit 213 to the non-contact power supply unit 309 is received by the control unit 306 of the power supply device 104, and the control unit 306 controls the power supply frequency of the power supplied from the internal power supply unit 305 to the non-contact power supply unit.

Figure 8:
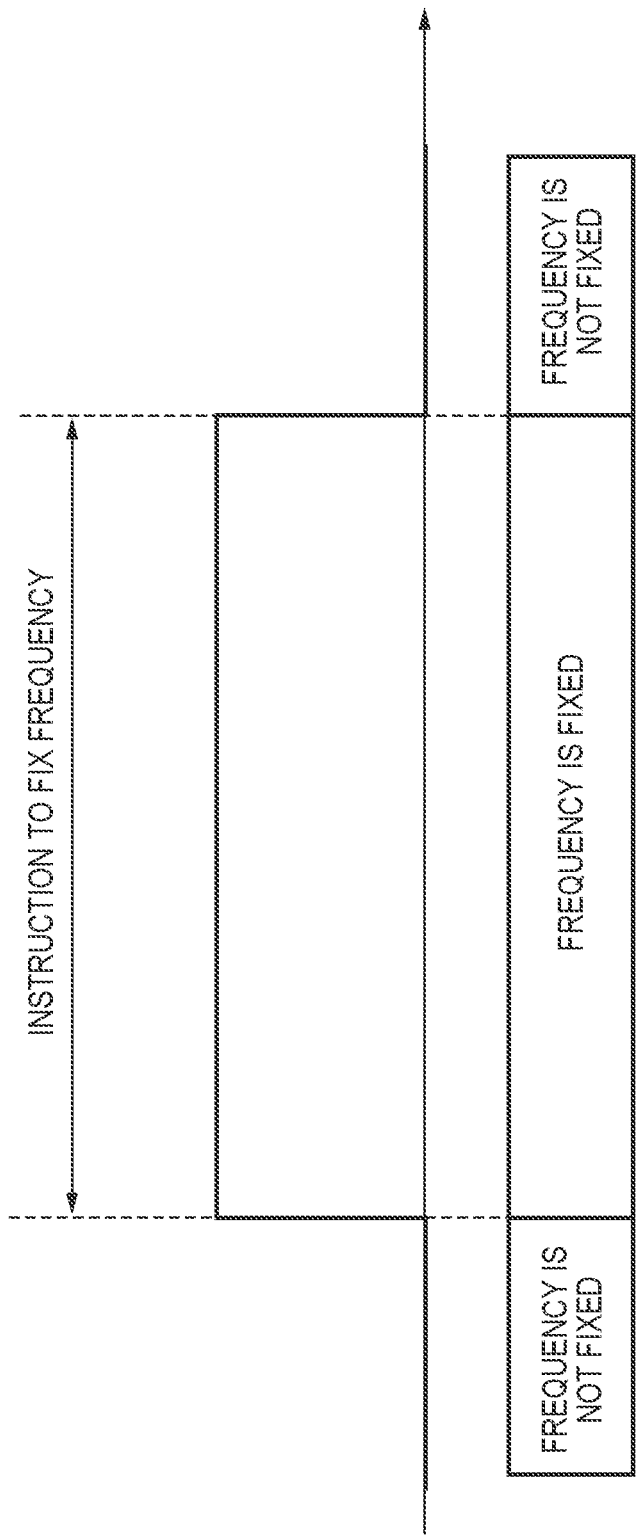
FIG. 8 is a diagram illustrating an example of communication that specifies a power supply frequency of the radiography system illustrated in FIG. 1.

The communication between the non-contact power supply unit 309 and the non-contact power receiving unit 213 may be performed, for example, using a Hi/Lo level in a 1-bit dedicated signal line, as illustrated in FIG. 8. Additionally, the physical layer of communication is not particularly limited, and for example, the communication may be performed by exchanging packets of instructions and responses for fixing and releasing the frequency, as illustrated in FIG. 9. Although information is described here as being exchanged using the non-contact power supply unit 309 and the non-contact power receiving unit 213, information may also be exchanged using the wired communication connection units 210 and 310, the wireless communication connection unit 209, the AP 105, and the like.

Once charges are accumulated by the sensor unit 201 for a predetermined amount of time, the radiography device 101 reads out signals in accordance with the accumulated charges (S606). As illustrated in FIG. 7, in the present embodiment, the radiography device 101 performs operations for accumulating charges for a predetermined amount of time in the sensor unit 201 and reading out signals in accordance with the accumulated charges (image capturing operations) twice in succession in order to correct a dark current component through offset correction. Image data for the offset correction in image capturing operations where no radiation was emitted is obtained by emitting radiation in either one of these two image capturing operations. Signals according to the charges accumulated through radiation emission are read out in the first instance. Next, the preparatory driving is performed for a predetermined amount of time, charges are accumulated the second time without emitting radiation, and the signals are read out. In order to correct the dark current component, the second accumulation time may be as close as possible to the first accumulation time. Additionally, the image data for correcting the dark current component may be obtained without emitting radiation in the first image capturing operations, and image data pertaining to the interior of the subject 110 may be obtained by emitting radiation in the second image capturing operations.

Once the second readout is complete, the control unit 204 of the radiography device 101 sends, to the power supply device 104, a signal for releasing the power supply frequency of the non-contact power supply from being fixed (S607). At this time, the signal for releasing the power supply frequency from being fixed may be transmitted to the power supply device 104 through the same path as in S605.

Then, the radiography device 101 sends image data on which correction processing and the like, such as predetermined offset correction, has been performed to the console 102 over the communication network 103 or the like, and completes the image capture (S608). The image data may be saved into the storage unit 205 rather than being sent to the console 102. If an instruction to turn the power of the radiography device 101 off has been made by the user operating the operation unit 207 (YES in S609), the radiography device 101 turns off, the sequence moves to S610, and the radiography device 101 enters a stopped state. On the other hand, if there is no instruction to turn the power of the radiography device 101 off (NO in S609), the sequence returns to S601, where the radiography device 101 stands by for the next image capture request. If the standby time is drawn out in S601, the radiography device 101 may enter a sleep state, in which power consumption is suppressed by turning off the display of the reporting unit 208 or the like, or the sequence may move to S610 and the power may be turned off.

In the present embodiment, the power supply device 104 continues supplying power to the radiography device 101 in the above-described two image capturing operations. At this time, the power supply device 104 supplies the power to the radiography device 101 at a constant power supply frequency during the period from when the radiography device 101 starts reading out the signals in the first image capturing operations to when the radiography device 101 finishes reading out the signals in the second image capturing operations.

The control unit 204 adjusts the time or the start timing of each operation so that the time from the start of the readout in the first image capturing operations to the start of the readout in the second image capturing operations is n×Tc (where n is a positive integer) for a period Tc of the fixed power supply frequency, as illustrated in FIG. 7. In other words, the control unit 204 performs control so that the time between the start of signal readout in the first image capturing operations and the start of signal readout in the second image capturing operations is a positive integral multiple of the period Tc of the power supply frequency. As an example, as illustrated in FIG. 7, the control unit 204 performs control so that the first accumulation time is a time Ti, the readout time is a time Tr, the preparatory driving time is a time Ts, and the second accumulation time is a time Ti'.

$$Tr+Ts+Ti'=n\times Tc \quad (1)$$

Because the times Tr and Ts are often fixed due to the time required for driving, Equation (1) is satisfied, for example, by adjusting the time Ti', which is the accumulation time in the second image capturing operations. In other words, the time for accumulating charges in the sensor unit 201 in the first image capturing operations and the time for accumulating charges in the sensor unit 201 in the second image capturing operations may be different from each other. However, for the purpose of offset correction, it is necessary for the time Ti and the time Ti' to be as close as possible. As such, the control unit 204 may control the radiography device 101 so that the time between the start of signal readout in the first image capturing operations and the start of signal readout in the second image capturing operations is the minimum positive integral multiple among the positive integral multiples of the period Tc of the power supply frequency. In non-contact power supply, the period Tc is often on the order of μsec or less, and when capturing radiographic images, the time Ti and time Ti' are generally of the order of msec or more. Therefore, adjusting the time Ti' is unlikely to affect the accuracy of the offset correction.

The control unit 204 may also adjust the timing using the preparatory driving time Ts instead of the time Ti'. In other words, the time Ts of the preparatory driving between the end of signal readout in the first image capturing operations and the start of charge accumulation in the sensor unit 201 in the second image capturing operations may be changed in accordance with the time Ti for charge accumulation in the sensor unit 201 in the first image capturing operations, the time Ti' for charge accumulation in the sensor unit 201 in the second image capturing operations, and the period Tc of the power supply frequency. For example, the control unit 204 may adjust the timing by making the time Ts of the preparatory driving longer than the minimum required time. In this case, the time for reading out the signal corresponding to the charge accumulated in the sensor unit 201 in the first image capturing operations and the time for reading out the signal corresponding to the charge accumulated in the sensor unit 201 in the second image capturing operations may be the same time. Additionally, using both the time Ti' and the time Ts, the control unit 204 may perform control so that the time between the start of signal readout in the first image capturing operations and the start of signal readout in the second image capturing operations is a positive integral multiple of the period Tc of the power supply frequency.

The control unit 204 may also control the power supply frequency of the non-contact power supply so that the period Tc satisfies the relationship in Tr+Ts+Ti'=n×Tc. The control unit 204 may determine the power supply frequency so that the time between the start of signal readout in the first image capturing operations and the start of signal readout in the second image capturing operations is a positive integral multiple of the period Tc of the power supply frequency, and then control the power supply device 104.

The power supply device 104 may be instructed of the period Tc or a frequency 1/Tc by the control unit 204 when the control unit 204 of the radiography device 101 sends the instruction to fix the frequency in S605. Additionally, the period Tc or the frequency 1/Tc used when the instruction to fix the frequency arrives may be set in the power supply device 104 in advance. The control unit 204 may also detect the power supply frequency from a periodic noise component of the signal read out in the first image capturing operations and adjust the lengths of the aforementioned Ts and Ti' in accordance therewith. The control unit 204 may determine the period Tc of the power supply frequency in accordance with image capturing conditions. For example, the control unit 204 may select a power supply frequency that enables power to be supplied more efficiently when capturing moving images than when capturing still images.

In the operations described above, the control unit 204 provided in the radiography device 101 is described as adjusting the period Tc of the power supply frequency, the time Ts of the preparatory driving, the length of the time Ti', which is the accumulation time of the second image capturing operations, and the like, but the configuration is not limited thereto. The radiation generation device console 107, the console 102, or the like may determine the lengths of the period Tc of the power supply frequency, the times Ts and Ti', and the like in accordance with the image capturing conditions for emitting radiation, which are input to the radiation generation device console 107 by the user. The period Tc of the power supply frequency, the times Ts and Ti', and so on determined by the radiation generation device console 107, the console 102, and the like are sent to the radiography device 101 and the power supply device 104. For example, the radiation generation device console 107, the console 102, or the like may be notified of the settings for the timings described above when the radiography device 101, the power supply device 104, or the like is started up. As illustrated in FIG. 1, a control device 180 may be provided in the radiography system 100, separate from the constituent elements described above, to control the radiography device 101, which is capable of receiving power in a non-contact manner, and the power supply device 104, which is capable of supplying power to the radiography device 101 in a non-contact manner.

Performing such control will result in noise of the same frequency being superimposed, at the same phase, on the image data obtained from the readout of the first image capturing operations and the image data obtained from the readout of the second image capturing operations. Accordingly, by performing offset correction, when reading out the signal generated by the sensor unit, the noise superimposed on the signal by changes in the electromagnetic field due to the operation of non-contact power supply are canceled out. During the period when, due to fluctuations in the power supply frequency at which the power supply device 104 supplies power to the radiography device 101, the signal obtained by the radiography device 101 from the sensor unit 201 is affected by the fluctuations in the power supply frequency, the power supply device 104 does not allow the frequency of the power supply to fluctuate. This suppresses a drop in the image quality of the obtained radiographic image. In addition, because the non-contact power supply is continuously performed even during image capture, a situation in which, for example, the internal power supply of the radiography device 101 runs out of charge during image capture and the image capture therefore cannot be continued is suppressed. In addition, because the non-contact power supply is continuously performed even during image capture, the capacity of the internal power supply of the radiography device 101 can be made smaller, and furthermore, because image capture can be performed even without having an internal power supply, the radiography device 101 can be made lighter and so on.

The fixing of the power supply frequency can be started any time before starting the readout in the first image capturing operations, and fixing can be released any time after the readout in the second image capturing operations is complete. However, because it is more power-efficient to vary the power supply frequency in accordance with fluctuations in the load of the radiography device 101, the period Tc of the power supply frequency may be fixed for the minimum necessary period, but it is necessary to take into account the response time for converging on the set frequency. A frequency that can respond to fluctuations in the load that may occur during the period when the power supply frequency is kept constant is set as the period Tc of the power supply frequency. Additionally, as mentioned above, it is more power-efficient to vary the power supply frequency in accordance with fluctuations in the load of the radiography device 101. Accordingly, outside the period from when the readout of the signals is started in the first image capturing operations to when the readout of the signals ends in the second image capturing operations, the power supply frequency of the power supplied from the power supply device 104 to the radiography device 101 can change as appropriate.

A radiography system according to some embodiments of the present invention will be described with reference to FIGS. 10 to 14. FIG. 10 illustrates an example of the configuration of the radiography system 100 according to a second embodiment of the present invention. The present embodiment will describe a case where, unlike in the first embodiment, the radiography system 100 operates in an emission detection capturing mode, in which the radiography device 101 and the radiation generation device 108 are not synchronized, and the radiography device 101 detects the start of radiation emission and captures an image. In the present embodiment, the radiography device 101 can detect the emission of radiation and shift to the image capturing operations. Therefore, there is no need to perform communication between the radiation generation device 108 and the radiography device 101, and thus the connecter 109 illustrated in FIG. 1 is unnecessary.

FIG. 11 illustrates an example of the configuration of the radiography device 101 according to the present embodiment. In addition to the constituent elements illustrated in FIG. 2, the radiography device 101 includes an emission detection unit 216 for detecting the start of radiation emission. There are multiple methods for realizing the emission detection unit 216, such as detection using a scintillator and a photodetector as with the sensor unit 201, or detecting the flow of current produced in the sensor unit 201 by radiation emission. The present embodiment will describe a method of obtaining electrical changes as radiation is incident on the radiography device 101. In other words, any method that includes a system using voltage or current (charge) for detection can be used. Accordingly, although the emission detection unit 216 is illustrated as a single functional unit in FIG. 11, the emission detection unit 216 may be integrated with the sensor unit 201 or the like.

Upon detecting that radiation has been emitted, the emission detection unit 216 notifies the control unit 204 of the start of radiation emission. In response to this notification, the control unit 204 controls the sensor unit 201, the sensor drive unit 202, and the reading unit 203 so that the electric charges produced by the radiation are accumulated in the sensor unit 201 and the signals corresponding to the electric charges are read out to generate image data after the radiation emission, in the same manner as in the foregoing first embodiment.

Figure 12A:
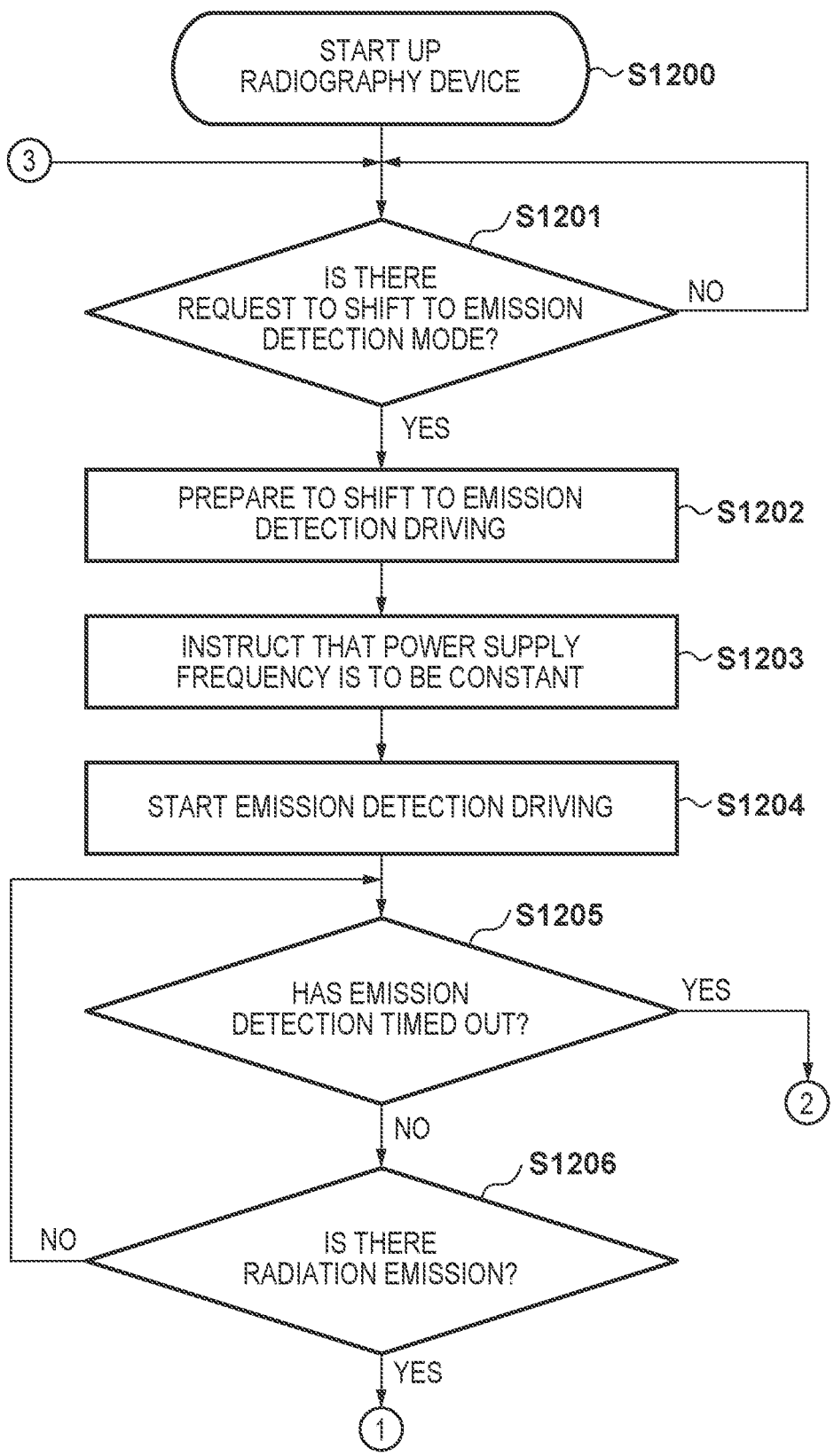
FIG. 12A is a flowchart illustrating processing performed when capturing an image in the radiography system illustrated in FIG. 10.
Figure 12B:
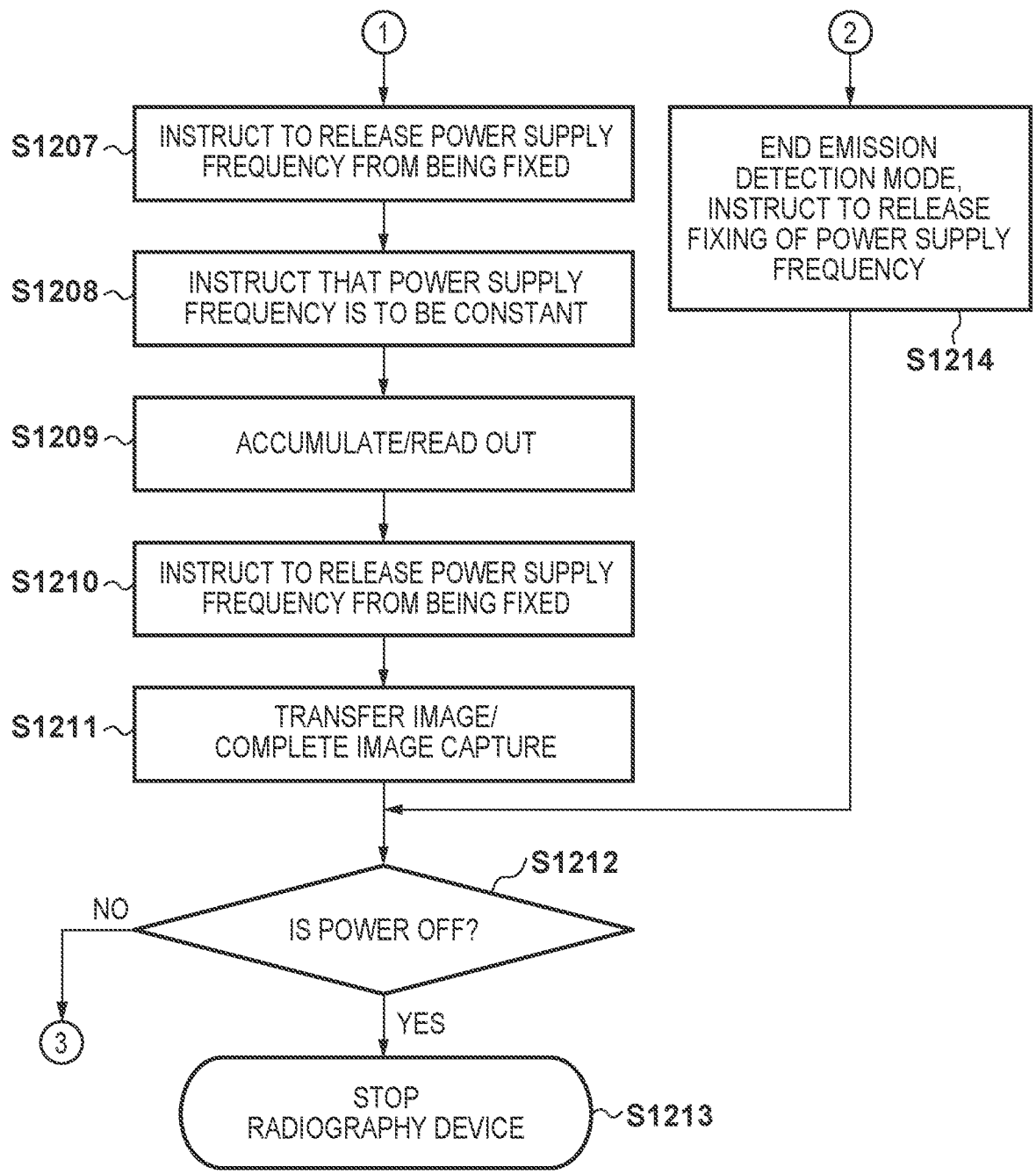
FIG. 12B is a flowchart illustrating processing performed when capturing an image in the radiography system illustrated in FIG. 10.
Figure 13:
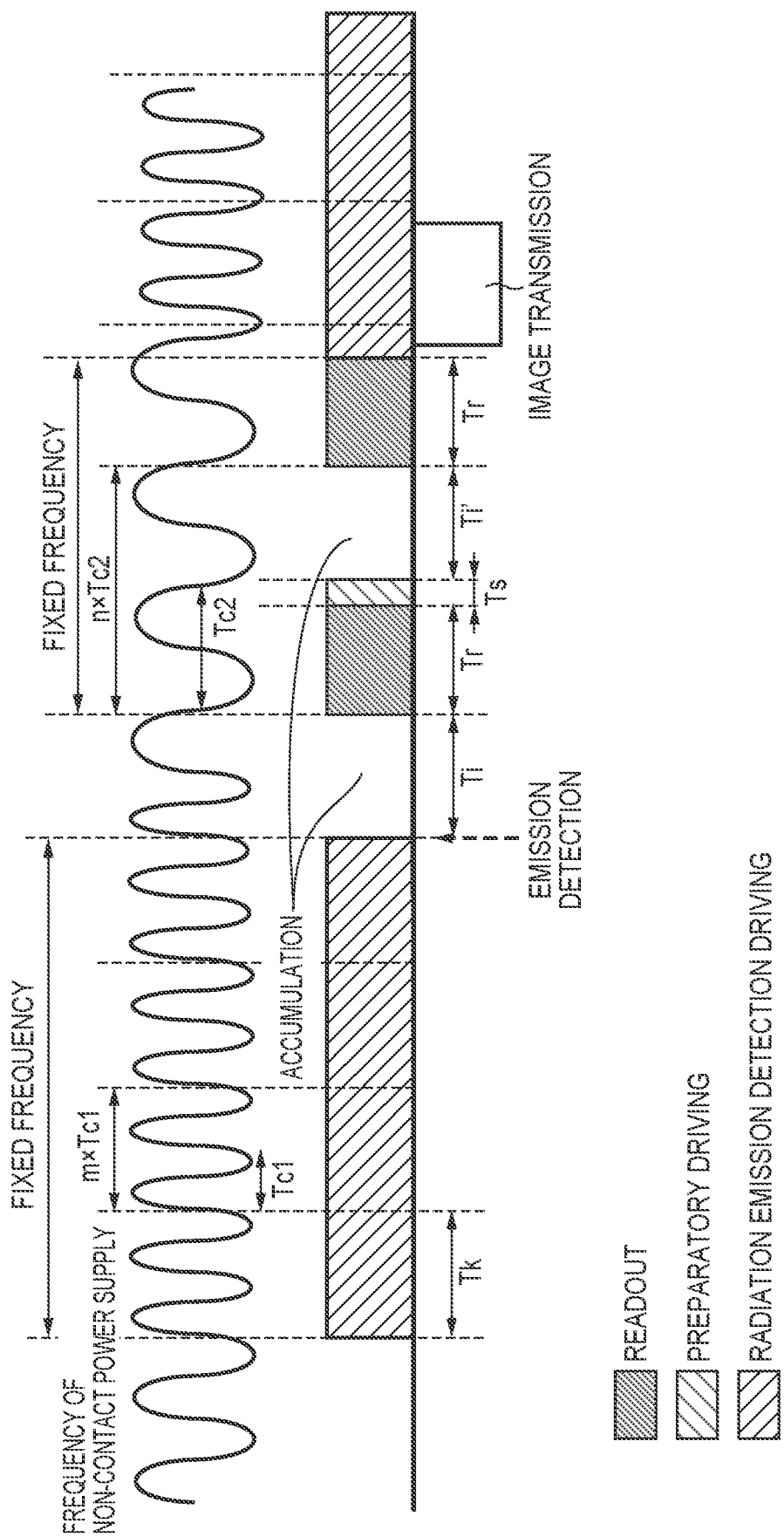
FIG. 13 is a timing chart illustrating operations performed when capturing an image in the radiography system illustrated in FIG. 10.

Operations of the radiography system 100 when performing non-contact power supply along with capturing a radiographic image in the emission detection capturing mode will be described next. In the present embodiment, while non-contact power supply is performed from the power supply device 104 to the radiography device 101, the frequency of the non-contact power supply is controlled so as not to vary during a period, before the image capturing operations, of operations for the emission detection unit 216 of the radiography device 101 to detect the start of radiation emission. As in the foregoing first embodiment, control is performed so that the frequency of the non-contact power supply does not fluctuate during the readout period of the image data. FIGS. 12A, 12B, and 13 are flowcharts and a timing chart, respectively, illustrating processing performed by the radiography system 100 when capturing an image in the emission detection capturing mode.

The process of S1200 immediately after the radiography device 101 is started up can be the same as S600 indicated in the flowchart in FIG. 6 in the synchronous capturing mode described above. Next, the process moves to S1201, where the control unit 204 determines whether or not there is a request to shift to image capture in the emission detection capturing mode, and if there is such a request, the sequence moves to S1202. Although the present embodiment assumes image capturing in the emission detection capturing mode, a configuration is also possible in which the mode can be switched between the above-described synchronous capturing mode and the radiation emission detection capturing mode, and processing for making the determination may be performed before S1201. An instruction to start an image capture sequence being made from the console 102 corresponding to the radiography device 101 is conceivable as one example of the request to shift to the emission detection capturing mode.

In S1202, preparatory processing such as powering and starting up functional units is performed in the radiography device 101 to shift to emission detection driving. The sequence then moves to S1203, where the control unit 204 sends a signal, instructing the power supply frequency of the non-contact power supply to not be allowed to fluctuate, to the power supply device 104 that performs non-contact power supply for the radiography device 101. The path, method, and the like for sending the signal can be the same as in the first embodiment.

The sequence then moves to S1204, where the radiography device 101 starts the emission detection driving. The control unit 204 sends an instruction to start the emission detection driving to the sensor drive unit 202, in response to which the sensor drive unit 202 performs emission detection driving for the sensor unit 201, and the control unit 204 sends an instruction to start the radiation emission detection operations to the emission detection unit 216. In the present embodiment, in the emission detection driving, the sensor unit 201 is scanned in the row direction while the emission detection unit 216 observes the voltage, current, and the like in the radiography device 101 that is sensitive to the presence or absence of radiation, changes in the intensity thereof, and the like.

In S1205, the control unit 204 determines whether or not a predetermined amount of time has been exceeded, and a timeout has occurred, in a state in which the emission detection driving is continued. Depending on the method for detecting radiation, it is possible to set a long detection waiting time. However, when considering the actual use of the radiography device 101, a timeout process may be provided for the time to detect radiation emission over a certain amount of time, so that the emission detection driving stops, in the event that the device is left as-is without any radiation being emitted.

If it is determined in S1205 that a predetermined timeout time has been reached, the sequence moves to S1212, where the emission detection capturing mode is ended, and the control unit 204 sends an instruction signal to release the fixing of the power supply frequency of the non-contact power supply (S1214). On the other hand, if it is determined in S1205 that the timeout time has not been reached, the sequence moves to S1206 to determine whether or not the emission of radiation has been started. In the present embodiment, the emission detection unit 216 performs necessary noise removal processing on the observed signals such as voltage and current, determines that radiation has been emitted when the signal exceeds a predetermined threshold, and notifies the control unit 204 to that effect. If no emission is determined to have occurred here, the sequence moves to S1205 again, and the processing loop is repeated until a timeout or until it is determined that radiation emission has started.

If it is determined in S1206 that radiation emission has started, the sequence moves to S1207, where the emission detection driving is ended. When the emission detection unit 216 determines that radiation has been emitted and the control unit 204 is notified, the control unit 204 causes the sensor drive unit 202 to stop the emission detection driving, and sends an instruction to start accumulating charges. In response, the sensor drive unit 202 puts the sensor unit 201 into a state in which charges can be accumulated in response to radiation. Additionally, the radiography device 101 sends an instruction signal to release the fixing of the power supply frequency of the non-contact power supply to the power supply device 104.

In the present embodiment, the emission detection driving is, as illustrated in FIG. 13, continuous driving of one period Tk, where one period is determined by the time it takes for the sensor array to make one scan in the row direction. During this period, operations of accumulating charges over a predetermined amount of time in a predetermined pixel of the sensor unit 201 for detecting radiation emission and reading out the signal corresponding to the accumulated charge is repeated. The sensor array may be driven not one row at a time, but a plurality of rows at once, and rather than being driven sequentially, for example, even-numbered rows may be driven first, and then odd-numbered rows may be driven thereafter. The voltage, current, or the like observed by the emission detection unit 216 may have a fixed pattern component superimposed thereon due to the characteristics of the sensor array or the like in the unit of the period Tk, and correction to remove this fixed pattern component is performed by taking a difference from the voltage, current, or the like one period previous. Here, setting the following equation for a period Tc1 of the non-contact power supply that is fixed during the emission detection driving for detecting the start of radiation emission results in the correction removing a periodic noise component, caused by the non-contact power supply, that is superimposed on the voltage, current, or the like.

$$Tk = m \times Tc1 \text{ (where } m \text{ is a positive integer)} \tag{2}$$

In other words, the control unit 204 performs control so that the period Tk at which the emission detection unit 216 detects the start of radiation emission in the detection operations (emission detection driving) is a positive integral multiple of the period Tc1 of the power supply frequency.

To satisfy Equation (2), the control unit 204 may adjust the driving time of the period Tk of the emission detection driving so that the period Tk becomes a positive integral multiple of the period Tc1. For example, FIG. 14 illustrates a case where N rows in a sensor array are driven sequentially from the first row to the last row in the emission detection driving, and when the driving of the last row is complete, the sensor array is driven sequentially again from the first row. The control unit 204 may provide a wait time Tw in which none of the rows are driven between the driving of the Nth row, which is the last row, and returning to drive the 0th line, which is the first line, and by adjusting the length of this wait time Tw, the period Tk may be adjusted to be an integral multiple of the period Tc1. In other words, the wait time Tw, which corresponds to a period Tc2 of the power supply frequency, may be provided during the readout operations for detecting the start of radiation emission, which are repeatedly performed by the emission detection unit 216. However, because no rows are driven during the period of the wait time Tw, no voltage or current is observed to detect the start of radiation emission, which makes the device insensitive to the detection of radiation emission. It is therefore necessary to make the wait time Tw as short a time as possible. Therefore, the control unit 204 controls the radiography device 101 so that the period Tk at which the emission detection unit 216 detects the start of radiation emission is the minimum positive integral multiple among the positive integral multiples of the period Tc1 of the power supply frequency. The control unit 204 may also adjust the period Tc1 so that Equation (2) is satisfied.

As in the foregoing first embodiment, the power supply device 104 may be instructed of the period Tc1 or a frequency 1/Tc1 by the control unit 204 when the control unit 204 of the radiography device 101 sends the instruction to fix the frequency. Additionally, the period Tc or the frequency 1/Tc used when the instruction to fix the frequency arrives may be set in the power supply device 104 in advance. When starting up the radiography device 101, the power supply device 104, or the like, a notification may be made from the console 102, the radiation generation device console 107, or the like. Additionally, information on the period Tk, the period Tc1, the wait time Tw, and the like may be sent as appropriate to the radiography device 101, the power supply device 104, or the like from a control device provided for controlling the non-contact power supply between the radiography device 101 and the power supply device 104.

The start of the fixation of the power supply frequency can be any time before the start of the emission detection driving, and the release of the fixation can be any time after the emission detection driving is completed. However, because it is more power-efficient to vary the power supply frequency in accordance with fluctuations in the load of the radiography device 101, the period Tc1 of the power supply frequency may be fixed for the minimum necessary period, but it is necessary to take into account the response time for converging on the set frequency. A frequency that can respond to fluctuations in the load that may occur during the period when the power supply frequency is kept constant is set as the period Tc1 of the power supply frequency. Additionally, as mentioned above, it is more power-efficient to vary the power supply frequency in accordance with fluctuations in the load of the radiography device 101. Accordingly, outside the period from when the readout of the signals is started in the first image capturing operations to when the readout of the signals ends in the second image capturing operations and the period in which the emission detection driving is performed, the power supply frequency of the power supplied from the power supply device 104 to the radiography device 101 can change as appropriate.

The subsequent image capturing operations (S1208 to S1211) and the power being turned off (S1212) to the stopping of the radiography device (S1213) can be the same processing and operations as in S605 to S610 described in the first embodiment. The processing and operations performed in S1208 to S1213 will therefore not be described here.

The period Tc1 of the power supply frequency in the emission detection driving and the period Tc2 of the power supply frequency between the start of signal readout in the first image capturing operations and the start of signal readout in the second image capturing operations may be the same, or may be different. In other words, the power supply frequency 1/Tc1 and the power supply frequency 1/Tc2 may be the same, or may be different from each other. For example, if the period of the power supply frequency is Tc1=Tc2=Tc', then it is necessary for m×Tc'=Tk and n×Tc'=Tr+Ts+Ti' (where m and n are positive integers) to be satisfied. In this case, the device may operate at the same power supply frequency period Tc' until S1210 without releasing the fixing of the power supply frequency in S1207. In other words, during the period from when the radiography device 101 starts the emission detection operations (emission detection driving) to when the signal readout in the second image capturing operations ends, the power supply device 104 may supply power to the radiography device 101 at the same power supply frequency.

For the preparatory driving after finishing the signal readout of the first image capturing operations indicated in FIG. 13, the sensor drive unit 202 may cause the sensor unit 201 to perform the same driving as the emission detection driving in order to remove the dark current component accurately. At this time, based on the voltage or current observed by operating the emission detection unit 216 too, the control unit 204 may calculate the period Tc2 of the noise caused by the non-contact power supply.

As described above, fluctuations in the frequency of the power supply can affect the detection of the start of radiation emission. Accordingly, during the period for detecting the start of radiation emission, the frequency of the power supply is controlled so as not to fluctuate. This enables power to be supplied from the power supply device 104 to the radiography device 101 while the radiography device 101 detects the start of radiation emission, even in the emission detection capturing mode in which the radiography device 101 and the radiation generation device 108 are not synchronized. Additionally, as in the foregoing first embodiment, power can be supplied from the power supply device 104 to the radiography device 101 while reading out the image data obtained by the sensor unit 201.

The present embodiment describes operations of accumulating charges over a predetermined amount of time in a predetermined pixel of the sensor unit 201 for detecting the start of radiation emission and reading out the signal corresponding to the accumulated charge. However, the configuration is not limited thereto, and the emission detection unit 216 may detect the start of radiation emission from changes in current flowing through an output signal line for reading out signals from the sensor unit 201, a bias line that supplies a bias voltage (driving voltage) to pixels provided in the sensor unit 201, or the like. Even in this case, fluctuations in the frequency of the power supply can affect the detection of the start of radiation emission. Accordingly, the power supply device 104 can supply power to the radiography device 101 at a constant power supply frequency even when the emission detection unit 216 detects the start of radiation emission from changes in current in the output signal line, the bias line, or the like. This enables power to be supplied from the power supply device 104 to the radiography device 101 while the radiography device 101 detects the start of radiation emission, even in the emission detection capturing mode in which the radiography device 101 and the radiation generation device 108 are not synchronized.

In this manner, in the foregoing embodiments, during the period when, due to fluctuations in the power supply frequency at which the power supply device 104 supplies power to the radiography device 101, the signal obtained by the radiography device 101 from the sensor unit 201 is affected by the fluctuations in the power supply frequency, the power supply device 104 supplies power to the radiography device 101 at a constant power supply frequency. The period during which the signal obtained by the radiography device 101 from the sensor unit 201 is affected by fluctuations in the power supply frequency can be the period during which the signal is read to generate a radiographic image, as described above. In the period for reading out signals to generate the radiographic image, the radiography device 101 causes the pixels of the sensor unit 201 to accumulate charges over a predetermined amount of time, and reads out signals according to the accumulated charges. Here, the period for accumulating charges in the pixels and reading out the signals according to the accumulated charges may be a period for accumulating charges generated by radiation emission and reading out the signals according to the accumulated charge in order to generate a radiographic image. The period for accumulating charges in the pixels and reading out the signals corresponding to the accumulated charges may be a period for obtaining image data for offset correction when generating a radiographic image. Additionally, the period during which the signal obtained by the radiography device 101 from the sensor unit 201 is affected by fluctuations in the power supply frequency can be a period for detecting the start of radiation emission. The start of radiation emission may be detected by reading out the signals according to the charges accumulated in the pixels provided in the sensor unit 201, or by detecting changes in current in signal lines, bias lines, or the like of the sensor unit 201. By performing such operations, the radiography system 100 according to the present embodiment can perform non-contact power supply from the power supply device 104 to the radiography device 101 at all times while suppressing effects on the image quality of the radiographic image and the accuracy of detecting the start of radiation emission.

A technique useful for performing non-contact power supply in a radiography system can be provided through the above-described configuration.

Other features and advantages of the present invention will be apparent from the following description taken in conjunction with the accompanying drawings. Note that the same reference numerals denote the same or like components throughout the accompanying drawings.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiography system comprising a radiography device and a power supply device, the radiography device including a sensor unit for obtaining a radiographic image and being capable of non-contact power reception, and the power supply device being capable of non-contact power supply to the radiography device,
wherein in a period in which a fluctuation in a power supply frequency of the power supply from the power supply device to the radiography device affects a signal obtained by the radiography device from the sensor unit, the power supply device is configured to supply power to the radiography device at a constant power supply frequency.

2. The radiography system according to claim 1, wherein the period in which the fluctuation of the power supply frequency affects the signal includes at least one of a period of reading out a signal for generating a radiographic image from the sensor unit or a period for detecting a start of radiation emission.

3. The radiography system according to claim 1, wherein the radiography device is configured to perform a first operation of reading out a signal from the sensor unit, and a second operation of reading out a signal from the sensor unit after the first operation; and
the power supply device is configured to supply power to the radiography device at a constant first power supply frequency during a period from when the radiography device starts reading out the signal in the first operation to when the radiography device stops reading out the signal in the second operation.

4. The radiography system according to claim 3, wherein the radiography device is configured to:
cause the sensor unit to accumulate a charge throughout a predetermined amount of time, and reads out a signal based on the accumulated charge, in the first operation; and
cause the sensor unit to accumulate a charge throughout a predetermined amount of time, and reads out a signal based on the accumulated charge, in the second operation, and
radiation is emitted in one of the first operation and the second operation.

5. The radiography system according to claim 3, wherein a first time from the start of readout of the signal in the first operation to the start of readout of the signal in the second operation is a positive integral multiple of a period of the first power supply frequency.

6. The radiography system according to claim 5, wherein the first time is a minimum positive integral multiple among the positive integral multiples of the period of the first power supply frequency.

7. The radiography system according to claim 3, wherein a time of accumulating a charge in the sensor unit in the first operation and a time of accumulating a charge in the sensor unit in the second operation are different from each other.

8. The radiography system according to claim 3, wherein a preparatory driving time from an end of readout of the signal in the first operation to a start of an accumulation of a charge in the sensor unit in the second operation changes according to a time in which a charge is accumulated in the sensor unit in the first operation, a time in which a charge is accumulated in the sensor unit in the second operation, and the period of the first power supply frequency.

9. The radiography system according to claim 3, wherein the power supply frequency of power supplied from the power supply device to the radiography device changes outside the period from when the radiography device starts reading out the signal in the first operation to when the radiography device stops reading out the signal in the second operation.

10. The radiography system according to claim 3, wherein the radiography device further includes an emission detection unit for detecting a start of radiation emission,
the radiography device is configured to perform a third operation including the first operation and the second operation in a predetermined pixel of the sensor unit, the third operation being performed before the start of radiation emission is detected by the emission detection unit, and
the power supply device is configured to supply power to the radiography device at the first power supply frequency while the radiography device performs the third operation.

11. The radiography system according to claim 10, wherein a period at which the emission detection unit detects the start of radiation emission in the third operation is a positive integral multiple of the period of the first power supply frequency.

12. The radiography system according to claim 10, wherein a period at which the emission detection unit detects the start of radiation emission in the third operation is a minimum positive integral multiple among positive integral multiples of the period of the first power supply frequency.

13. The radiography system according to claim 10, wherein a wait time corresponding to the period of the first power supply frequency is provided during a readout operation for detecting the start of radiation emission repeatedly performed by the emission detection unit.

14. The radiography system according to claim 3, wherein the radiography device further includes an emission detection unit for detecting a start of radiation emission, the radiography device is configured to perform a third operation of causing the emission detection unit to detect the start of radiation emission before performing the first operation, and the power supply device is configured to supply power to the radiography device at a constant second power supply frequency while the radiography device performs the third operation.

15. The radiography system according to claim 14, wherein a period at which the emission detection unit detects the start of radiation emission in the third operation is a positive integral multiple of the period of the second power supply frequency.

16. The radiography system according to claim 14, wherein a period at which the emission detection unit detects the start of radiation emission in the third operation is a minimum positive integral multiple among positive integral multiples of the period of the second power supply frequency.

17. The radiography system according to claim 14, wherein a wait time corresponding to the period of the second power supply frequency is provided during a readout operation for detecting the start of radiation emission repeatedly performed by the emission detection unit.

18. The radiography system according to claim 14, wherein the first power supply frequency and the second power supply frequency are mutually-different frequencies.

19. The radiography system according to claim 14, wherein the first power supply frequency and the second power supply frequency are the same frequency, and the power supply device is configured to supply power to the radiography device at the same power supply frequency during a period from when the radiography device starts the third operation to when the radiography device finishes reading out the signal in the second operation.

20. The radiography system according to claim 14, wherein the power supply frequency of the power supplied from the power supply device to the radiography device changes in accordance with a load of the radiography device outside the period from when the radiography device starts reading out the signal in the first operation to when the radiography device stops reading out the signal in the second operation and a period in which the third operation is performed.

* * * * *